(12) United States Patent
Archibald et al.

(10) Patent No.: US 11,730,479 B2
(45) Date of Patent: *Aug. 22, 2023

(54) DEVICES AND METHODS FOR NERVE REGENERATION

(71) Applicant: Integra LifeSciences Corporation, Princeton, NJ (US)

(72) Inventors: Simon J. Archibald, Pennington, NJ (US); Fergal O'Brien, Dublin (IE); Amos Matsiko, Dublin (IE)

(73) Assignee: Integra LifeSciences Corporation, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/520,987

(22) Filed: Nov. 8, 2021

(65) Prior Publication Data

US 2022/0054134 A1 Feb. 24, 2022

Related U.S. Application Data

(63) Continuation of application No. 16/465,663, filed as application No. PCT/US2017/064499 on Dec. 4, 2017, now Pat. No. 11,179,157.

(60) Provisional application No. 62/429,363, filed on Dec. 2, 2016.

(51) Int. Cl.
| | | |
|---|---|---|
| A61L 27/26 | (2006.01) | |
| A61L 27/56 | (2006.01) | |
| A61L 27/24 | (2006.01) | |
| A61B 17/11 | (2006.01) | |
| A61B 17/04 | (2006.01) | |
| A61L 27/54 | (2006.01) | |
| A61B 17/00 | (2006.01) | |

(52) U.S. Cl.
CPC .......... *A61B 17/1128* (2013.01); *A61L 27/24* (2013.01); *A61L 27/26* (2013.01); *A61L 27/54* (2013.01); *A61L 27/56* (2013.01); *A61B 2017/00004* (2013.01); *A61B 2017/1132* (2013.01); *A61L 2300/236* (2013.01); *A61L 2300/252* (2013.01); *A61L 2430/32* (2013.01)

(58) Field of Classification Search
CPC ...... A61B 17/1128; A61B 2017/00004; A61B 2017/1132; A61L 27/24; A61L 27/26; A61L 27/54; A61L 27/56; A61L 2300/236; A61L 2300/252; A61L 2430/32
See application file for complete search history.

(56) References Cited

U.S. PATENT DOCUMENTS

| | | |
|---|---|---|
| 4,778,467 A | 10/1988 | Stensaas et al. |
| 4,877,029 A | 10/1989 | Valentini et al. |
| 4,955,893 A | 9/1990 | Yannas et al. |
| 4,963,146 A | 10/1990 | Li |
| 5,011,486 A | 4/1991 | Aebischer et al. |
| 5,019,087 A | 5/1991 | Nichols |
| 5,026,381 A | 6/1991 | Li |
| 5,092,871 A | 3/1992 | Aebischer et al. |
| 5,502,092 A | 3/1996 | Barrows et al. |
| 5,656,605 A | 8/1997 | Hansson et al. |
| 5,925,053 A | 7/1999 | Hadlock et al. |
| 5,948,654 A | 9/1999 | Tranquillo et al. |
| 5,997,895 A | 12/1999 | Narotam et al. |
| 6,057,137 A | 5/2000 | Tranquillo et al. |
| 6,214,021 B1 | 4/2001 | Hadlock et al. |
| 6,447,701 B1 | 9/2002 | Heschel et al. |
| 6,461,629 B1 | 10/2002 | Tranquillo et al. |
| 6,899,873 B2 | 5/2005 | Ma et al. |
| 6,969,523 B1 | 11/2005 | Mattern et al. |
| 7,198,799 B2 | 4/2007 | Mueller et al. |
| 10,940,235 B2 | 3/2021 | Kohn et al. |
| 11,179,157 B2 * | 11/2021 | Archibald |
| 2001/0031974 A1 | 10/2001 | Hadlock et al. |
| 2002/0018799 A1 | 2/2002 | Spector et al. |
| 2002/0150753 A1 | 10/2002 | Ma et al. |
| 2003/0176876 A1 | 9/2003 | Chen et al. |
| 2005/0013844 A1 | 1/2005 | Hadlock et al. |
| 2011/0129515 A1 | 6/2011 | Archibald |
| 2015/0073564 A1 | 3/2015 | Valmikinathan et al. |

FOREIGN PATENT DOCUMENTS

| | | |
|---|---|---|
| WO | WO-2011047970 A1 | 4/2011 |
| WO | WO-2016077839 A1 | 5/2016 |

OTHER PUBLICATIONS

Feb. 2, 2018—International Search Report and Written Opinion of PCT/US2017/064499.
Abstract of "Development of a Neural Matrix for Enhanced Peripheral Nerve Repair," Wang, et al., Tissue Engineering Society International, 2003, Annual Meeting, Orlando, Florida.
Anonymous. Science Learning Hub [online]; 2007; downloaded from <URL https://www.sciencelearn.org.nz/resources/1006- insulation> on Nov. 19, 2018; 6 pages. (Year: 2007).
Damink et al. J Mater Sci Mater Med. 1995; 6: 460-472. (Year: 1995).
European Search Report issued from corresponding EP Application No. 10163973.0, dated Nov. 26, 2013.
Harley et al. Cells Tissues Organs.2004; 176(1-3): abstract. (Year: 2004).

(Continued)

*Primary Examiner* — Alma Pipic
(74) *Attorney, Agent, or Firm* — Eva Tan

(57) ABSTRACT

The present invention is directed to a nerve regeneration conduit including a resorbable tube having a matrix therein. The matrix is characterized by substantially parallel, axially aligned pores extending the length of the matrix. The matrix is formed by the axial freezing of a slurry having little or no significant radial thermal gradient during the freezing process. The matrix is used to bridge the gap between the severed ends of a nerve and provide a scaffold for nerve regeneration.

20 Claims, 23 Drawing Sheets

(56) References Cited

OTHER PUBLICATIONS

Hattori "Alkali-Treated Collagen Retained the Triple Helical Conformation and the Ligand Activity for the Cell Adhesioin via a2b1 Integrin" Journal of Biochemistry. vol. 125. pp. 676-784. (1999); Abstract P..676 Retrieved from https://www.jstage.jst.go.jp/article/biochemistry1922/125/4/125_4_676/_pdf/-char/en.

Sakamoto, "Further Development of Scaffolds for Regneration of Nerves," Medical Design Briefs, May 2009.

Paul et al. "Chemical Stabilisation of Collagen as a Biomimetic", The Scientific World Journal (2003) 3; 138-155.

Evercooren et al. Nerve growth factor, laminin, and fibronectin promote neurite growth in human fetal sensory ganglia cultures. J. Neurosci. Res., 8: 179-193, 1982 (Year: 1982).

Plantman et al. Integrin-laminin interactions controlling neurite outgrowth from adult DRG neurons in vitro. Molecular and Cellular Neurosicence. vol. 39, Issue 1, 2008, pp. 50-62 (Year: 2008).

Spearman et al. Tissue-Engineered Peripheral Nerve Interfaces. Advanced Functional Materials. 2017, 1701713 (Year: 2017).

Dyck et al. Chondroitin sulfate proteoglycans: Key modulators in the developing and pathologic central nervous system. Experimental Neurology 269 (2015) 169-187 (Year: 2015).

Chawla. Peripheral Nervous System Anatomy, Medscape, 2016 (Year: 2016).

Haugh et al. Novel Freeze-Drying Methods to Produce a Range of Collagen-Glycosaminoglycan Scaffolds with Tailored Mean Pore Sizes. Tissue Engineering. vol. 16, No. 5, 2010 (Year: 2010).

Rolls et al. PLOS Medicine. 2008; 5(8): 1262-1277. (Year:2008).

Ding Tan et al. Rapid Repair of rat sciatic nerve injury using a nanosilver-embedded collagen scaffold coated with laminin and fibronectin. Regenerative Medicine, Future Medicine Ltd, GB, vol. 6, No. 4, pp. 437-447 (Year 2011).

* cited by examiner

Cross section magnification 15X

Cross section magnification 100X

Longitudinal cross section magnification 150X

DEVICES AND METHODS FOR NERVE REGENERATION

CROSS REFERENCE SECTION

This application is a continuation of and claims priority and benefit under 35 U.S.C. § 120 to copending U.S. patent application Ser. No. 16/465,663, which is a National Stage Application under 35 U.S.C. § 371 of PCT Application No. PCT/US17/64499, filed Dec. 4, 2017, which claims priority and benefit to U.S. Provisional Application No. 62/429,363 filed on Dec. 2, 2016, all of which are incorporated herein by reference in their entirety.

FIELD OF THE INVENTION

The present invention relates to the field of mammalian nerve regeneration. Specifically, the present invention relates to methods of making devices useful for nerve regeneration. The present invention further relates to devices and methods that assist in regenerating a severed peripheral nerve by bridging the gap between the ends of the severed peripheral nerve and providing a scaffold to support regrowth of nerve tissue.

BACKGROUND

Nerve regeneration conduits are known. See U.S. Pat. No. 5,019,087. Methods for making nerve regeneration prostheses are also known. See U.S. Pat. No. 4,955,893 and US Patent Application Publication No. 2011/0129515. However, it is desirable to promote regeneration of nerve tissue to rejoin the ends of severed nerves.

It is therefore an object of the present invention to provide a regenerative scaffold to enhance axon and Schwann cell propagation during the process of peripheral nerve regeneration across nerve gaps greater than allowed by prior entubulation repair techniques. It is also an object of the present invention to provide an apparatus and process that allows the routine manufacture of a biocompatible nerve regeneration conduit comprising a resorbable tube filled with a resorbable matrix having controlled pore size and parallel, axially oriented pore alignment resembling the Schwann cell basal lamina.

It is also an object of the present invention to provide a collagen-based conduit filled with a resorbable matrix that includes inductive macromolecules to enhance the regenerative potential of the conduit. Such a capability has the potential for enhancing regenerative capacity for large gap defects from injuries or other trauma. These and other objects, features, and advantages of the invention or certain embodiments of the invention will be apparent to those skilled in the art from the following disclosure and description of exemplary embodiments.

SUMMARY

Embodiments of the present invention are directed to nerve guides and are further directed to devices and methods for tissue regeneration and, in particular, nerve tissue regeneration using a scaffold of the present invention. According to certain aspects of the present invention, a method is provided in which axial freezing of a suspension, dispersion or slurry (collectively "slurry") having little or no significant radial thermal gradient followed by freeze drying results in a matrix having a plurality of passages, channels, pathways or pores (collectively, "pores") generally spanning one end of the matrix to the other. In one embodiment of the method, the slurry is thermally insulated to provide it with little or no significant radial thermal gradient during the axial freezing of the slurry. The terms dispersion, slurry and suspension are used interchangeably herein.

The configuration of pores produced by methods of the present invention that span one end of the matrix to the other promotes the growth of tissue, and more specifically nerve tissue, into and through the matrix as a whole, as physical obstructions within the pores in the matrix are minimized by the method of the present invention. The pores can be axially-oriented to the extent that the pores allow nerve tissue to grow into and through the matrix. The pores can be axially-oriented that span one end of the inner matrix to the other and the outer collagen-based tube or conduit can be configured with pores that span one end of the outer tube or conduit to the other. Such pores are directed along the axis of the severed nerve and promote the growth of the nerve tissue into and through the pores of the matrix scaffold.

According to one aspect of the present invention, the matrix allows nerve tissue to grow from opposite ends of the matrix and join together at a point within the matrix, as a characteristic of a plurality of pores is that they span one end of the matrix to the other in an unobstructed manner. In an exemplary embodiment, a severed nerve can be reconnected by interconnecting each severed end of the nerve with the matrix of the present invention and allowing nerve tissue to grow through the matrix from opposite ends until contacting and combining together and, preferably, forming a functioning nerve where it was once severed and nonfunctioning. In this manner, embodiments of the present invention include a prosthesis or implant or scaffold to regenerate damaged nerve fibers that have a gap or distance between the severed ends of the nerve fibers. The prosthesis or implant or scaffold or conduit can be made to have different diameters and/or lengths, as desired, for use with different diameter nerve and different gaps or distances between severed nerves. The prosthesis or implant or scaffold or conduit of the present invention are also capable of showing increased fatigue resistance following cyclic compression.

According to embodiments of the present invention, the step of maintaining the suspension at little or no significant radial thermal gradient while axially freezing the suspension followed by freeze drying optimizes the formation of axially oriented pores. The greater the number and consistency of axially oriented pores within the matrix from one end of the matrix to the other, the greater the ability of the matrix to allow, and even promote, nerve growth therein and therethrough.

According to alternate embodiments of the present invention, the matrix is useful as a device by itself, and can be combined with one or more connectors such as cuffs to allow the joining of the matrix to respective ends of a severed nerve. According to a different embodiment, the matrix can be preformed and then inserted into and housed by a hollow conduit. Alternatively, a suspension can be introduced into a conduit or hollow conduit/tube which is maintained at little or no significant radial thermal gradient and then the suspension can be axially frozen followed by freeze drying to form the matrix within the conduit/tube. In either embodiment, the conduit housing the matrix can likewise be combined with one or more connectors, such as cuffs to allow the joining of the matrix to respective ends of a severed nerve. Still alternatively, the end portions of the conduit may be hollow, may lack matrix or otherwise may extend beyond the matrix therein to allow the severed end of a nerve to be inserted into the conduit in a manner to contact the matrix and allow nerve growth therein.

DETAILED DESCRIPTION OF CERTAIN EXEMPLARY EMBODIMENTS

Figure 1:
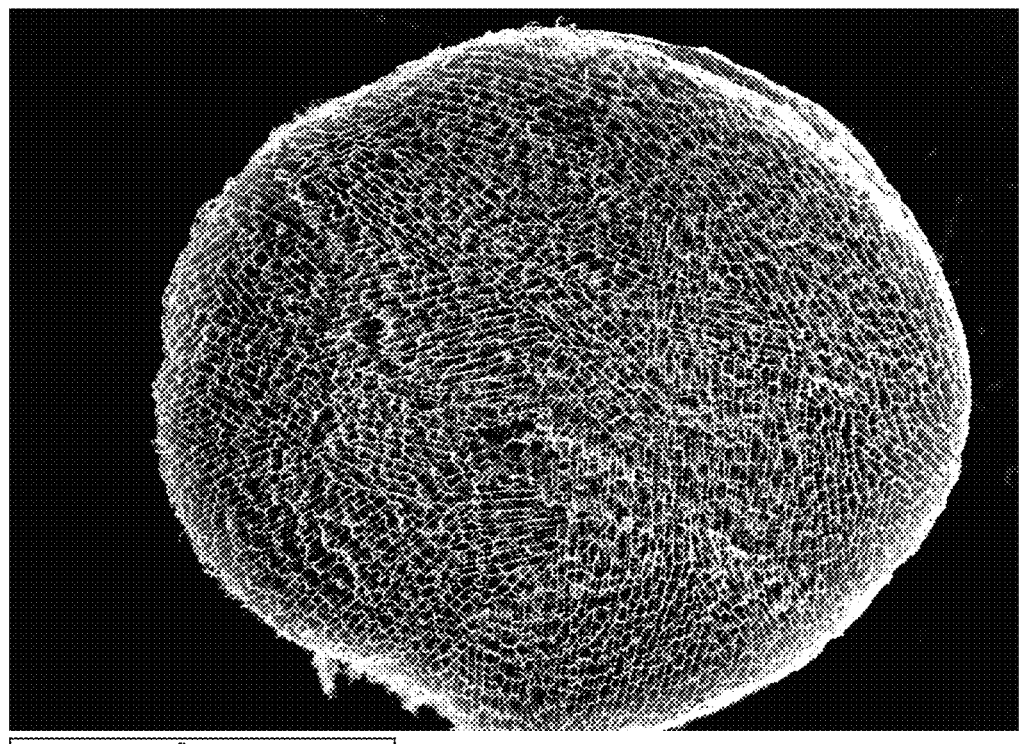
FIG. 1 is a scanning electron micrograph at 15× of a cross-section of a matrix produced by the method of the present invention.

Embodiments of the present invention are based on the discovery of a device and method that produces axially aligned pores in a matrix using a slurry having little or no significant radial thermal gradient during axial freezing of the slurry. In one embodiment, the slurry is thermally insulated to maintain little or no significant radial thermal gradient during axial freezing. The term "little or no significant radial thermal gradient" means no detectable thermal gradient in the radial direction of the slurry or at the very least any thermal gradient that exists does not adversely affect the formation of axially aligned pores. For purposes of exemplary embodiments of the present invention, little or no significant radial thermal gradient is achieved by insulating the slurry during axial freezing of the slurry. Without being bound by any scientific theory, axial freezing of the slurry having little or no significant radial thermal gradient is believed to produce axially aligned ice crystals along the length of the slurry. Freeze drying removes the crystals and leaves behind a matrix having axially aligned pores.

In accordance with a first aspect of the invention, the slurry used to form the matrix includes materials known to those of skill in the art used to form such matrices. The materials include biocompatible and/or bioresorbable materials that can form a liquid slurry or suspension. Such materials or macromolecules include collagen, laminin, fibronectin, merosin (also referred to as laminin-2), hyaluronic acid, chitin, chitosan, keratin, polyglycolic acid, polylactic acid, cellulose and the like. The materials can be used alone or in combination with each other. It is to be understood that the list of materials is not exhaustive and that one of skill in the art will readily identify other materials useful to make slurries based on the present disclosure. In certain exemplary embodiments, the matrix is formed from collagen. Collagen is a fibrous protein and constitutes the major protein component of skin, bone, tendon, ligament, cartilage, basement membrane and other forms of connective tissue. Collagen is biodegradable, and when implanted in the body, is absorbed at a rate that can be controlled by the degree of intra- or intermolecular cross-linking imparted to the collagen molecule by chemical or physical treatment. Thus upon implantation, the collagen matrix can be designed to be absorbed as the tissue grows into the matrix, such as when nerve tissue regenerates and grows into the matrix.

In certain exemplary embodiments, the matrix includes collagen and at least one glycosaminoglycan. Exemplary glycosaminoglycans include chondroitin sulfate, (chondroitin-6-sulfate proteoglycan), dermatan sulfate, keratin sulfate, hyaluronic acid, and the like. The glycosaminoglycans can be used alone or in combination with each other. It is to be understood that the list of glycosaminoglycans is not exhaustive and that one of skill in the art will readily identify other materials useful to make slurries based on the present disclosure. In certain exemplary embodiments, the collagen and the glycosaminoglycan are cross-linked. Cross-linking can be achieved by heating under vacuum or by treatment with chemical cross-linking agents, e.g., glutaraldehyde, formaldehyde, chromium sulfate, carbodiimide, adipyl dichloride, and the like.

The materials to form the matrix are combined with a liquid to form a slurry which is then introduced into a mold to form a matrix of a desired shape. Suitable liquids within the scope of the invention should be capable of being removed by freeze drying and include water, and aqueous fluids containing alcohol, acetic acid and the like. The liquids can be used alone or in combination with each other. It is to be understood that the list of liquids is not exhaustive and that one of skill in the art will readily identify other materials useful to make slurries based on the present disclosure. Methods of freeze drying materials that contain liquids such as water are known to those of skill in the art.

Other materials can be included into or otherwise form the slurry and therefore can be incorporated into the matrix as desired. Such other materials include drugs, growth factors, extracellular matrix components, fibrous materials and the like. The other materials can be used alone or in combination with each other. It is to be understood that the list of other materials is not exhaustive and that one of skill in the art will readily identify still other materials based on the present disclosure.

Other materials that can be included or otherwise form the slurry include inductive macromolecules from the basal lamina. The inductive macromolecules play a significant role in the nerve regeneration process in terms of soliciting guidance, proliferation axonal growth and remyelination (Wallquist et al., 2005, Bunge et al., 1986, Buttery and ffrench-Constant, 1999). The term inductive macromolecules can include, but is not limited to glycosaminoglycans such as hyaluronans, chondroitin sulfate, dermatan sulfate, heparin sulfate, keratin sulfate, proteoglycans such as aggrecan, decorin, syndecans, as well as collagen, elastin, fibronectin, laminin-1 and laminin-2, and other growth factors. Preferably, fibronectin in combination with laminin-1 and laminin-2 has shown an unexpected and surprising synergy capable of promoting Schwann cell migration and growth, as well as axonal growth from dorsal root ganglions (DRGs). In certain exemplary embodiments, the inductive macromolecules are cross-linked. Cross-linking can be achieved by heating under vacuum or by treatment with chemical cross-linking agents, e.g., glutaraldehyde, formaldehyde, chromium sulfate, carbodiimide, adipyl dichloride, and the like.

It is to be understood that molds of any desired shape can be used in the present invention based upon the principles disclosed herein and for use where it is desired that tissue grow into the pores of the matrix. Particular molds can be used to produce various desired matrix shapes including tubes, cylinders, rectangles, spheres, sheets and other desired shapes and can even be in the same general shape as wound sites or tissue defects so that the matrix can be fit to the particular wound site or tissue defect. Although the matrices of the present invention can be used to regenerate and connect severed nerves, the matrices also have other uses where reconnecting severed or broken tissue or rebuilding damaged tissue through tissue regeneration would be advantageous. Such applications include regeneration of tendon, articular cartilage, bone, corticospinal tracts, and other linearly aligned structures.

An exemplary mold can produce a single matrix or a mold may be capable of producing a plurality of matrices, such as where the mold includes a plurality of chambers of desired design into which the slurry can be introduced and then subject to axial freezing. Such a mold contemplates commercial manufacture of the matrices of the present invention where it is desired to mass produce such matrices in a batch format. Individual chambers within a mold are insulated so the slurry therein has little or no significant thermal gradient during axial freezing. Each individual chamber can include an insulating material therein surrounding the chamber or the entire mold can be formed from an insulating material thereby insulating the slurry in the individual chambers. Suitable insulating materials include STYROFOAM, AEROGEL and the like.

According to an additional exemplary embodiment, the matrix can be used by itself or it can be preformed and then inserted into a hollow conduit for use as a prosthesis. Alternatively, the matrix can be formed directly inside a hollow conduit. According to this embodiment, a slurry is placed into a hollow conduit or outer tube which is insulated. The axial freezing process and freeze drying process takes place to form the matrix within the conduit. The conduit containing the matrix is then used as a prosthetic device to connect severed tissue. In one embodiment, the conduit is biodegradable or bioresorbable. An exemplary period of time for biodegradability or bioresorbability is within about 1 to about 3 months. An exemplary embodiment is a resorbable collagen tube, as is commercially available under the brand name NEURAGEN from Integra LifeSciences Corporation, Plainsboro, N.J. Methods for making certain exemplary embodiments of the resorbable tube are disclosed in U.S. Pat. No. 5,019,087, which is incorporated herein by reference in its entirety.

In certain exemplary embodiments, the collagen in the resorbable tube is Type I collagen, and the tube further comprises a laminin-containing material. Laminin is a glycoprotein that is an abundant component of all basement membranes. As used herein, the phrase "laminin-containing material" is meant to include purified laminin itself or a material which contains laminin and other basement membrane components and is capable of forming a dispersion from which the resorbable tubes are made. Materials which contain laminin include basement membranes, human placenta, and an extract of a mouse sarcoma known in the art as Matrigel. In certain exemplary embodiments, the amount of Type I collagen that is combined with the laminin present in the laminin-containing material on a dry weight basis is in the ratio of about 90:10 to 40:60. In certain exemplary embodiments other optional additives which may aid in the nerve regeneration may also be present in the resorbable tube in addition to collagen, for example, heparin, heparan sulfate proteoglycan, glycosaminoglycans such as hyaluronic acid, chondroitin sulfate and others, growth hormones such as epidermal growth factor (EGF), nerve growth factor, glycoproteins such as fibronectin, and the like. The glycosaminoglycans can be used alone or in combination with each other. It is to be understood that the list of optional additives is not exhaustive and that one of skill in the art will readily identify other optional additives useful in the present invention based on the present disclosure.

In certain exemplary embodiments, the resorbable tube may be cross-linked. This can be done with chromium sulfate, formaldehyde, glutaraldehyde, carbodiimide, adipyl dichloride, and the like. The rate at which the resorbable tube of the present invention is resorbed in vivo in a mammal is dependent on the degree of cross-linking. Factors controlling the extent of crosslinking are the type and concentration of the cross-linking agent, the pH, and the temperature of incubation. In certain exemplary embodiments, the nerve regeneration conduits of the present invention are cross-linked to such an extent that they are completely resorbed within about 1 to about 3 months.

In certain exemplary embodiments, the resorbable tube/outer tube or conduit has a length of about 1 cm to about 15 cm, and an inner diameter in the range of from about 1 mm to about 1.5 cm. The length of the resorbable tube/outer tube or conduit may vary with the length of the nerve gap to be bridged, and the inner diameter may vary with the diameter of the nerve. In certain exemplary embodiments, the resorbable tube/outer tube or conduit has a length of about 1 cm to about 15 cm or 2 cm to about 10 cm, e.g., a length of about 2 cm to about 4 cm, a length of about 3 cm to about 7 cm. In certain exemplary embodiments, the inner diameter of the resorbable tube/outer tube or conduit is in the range from about 1 mm to about 15 mm, e.g., from about 1.5 mm to about 10 mm or about 1.5 mm to about 5.0 mm. The wall thickness of the resorbable tube represents a balance between desired permeability and enough compressive strength to prevent collapse. Preferably, the tubes are made as thin as possible while still withstanding suturing and collapse when used in vivo. In certain exemplary embodiments, the resorbable tube has a wall thickness in the range of from about 0.2 mm to about 1.2 mm, e.g. about 0.1 mm to about 0.8 mm. In certain exemplary embodiments, the resorbable tube is less porous than the matrix.

According to another exemplary embodiment of the present invention, an outer collagen tube is formed. The outer collagen tube or conduit is hollow. According to certain exemplary embodiments, the collagen in the resorbable tube or conduit is Type I collagen. According to another exemplary embodiment, the collagen in the resorbable tube or conduit is alkali-treated (AT) collagen.

According to another exemplary embodiment, the tube further comprises a laminin-containing material. In certain exemplary embodiments, the amount of Type I collagen that is combined with the laminin present in the laminin-containing material on a dry weight basis is in the ratio of about 90:10 to 40:60.

According to another exemplary embodiment, the collagen tube is filled with a slurry to form an internal matrix. In certain exemplary embodiments, the slurry includes collagen, chondroitin sulfate, and one or more inductive macromolecules. Preferably, the inductive macromolecules include fibronectin, laminin-1, or laminin-2. In certain exemplary embodiments, the amount of fibronectin, laminin-1, or laminin-2 combined on a dry weight basis is in the ratio of about 1:1 if two macromolecules are used. In certain exemplary embodiments, the amount of chondroitin sulfate, fibronectin, laminin-1, and laminin-2 combined on a dry weight basis is in the ratio of about 1:1:1:1. In certain exemplary embodiments, the concentration of chondroitin sulfate, fibronectin, laminin-1, and laminin-2 is about 5 µg/ml for each component. In certain exemplary embodiments, the concentration of chondroitin sulfate, fibronectin, laminin-1, and laminin-2 is about 1-5 µg/ml for each component. In certain exemplary embodiments, the concentration of chondroitin sulfate, fibronectin, laminin-1, and laminin-2 is about 5-10 µg/ml for each component. In certain exemplary embodiments, the concentration of chondroitin sulfate, fibronectin, laminin-1, and laminin-2 is about 1-10 µg/ml for each component. In certain exemplary embodiments, the slurry further includes a glycosaminoglycan such as dermatan sulfate, keratin sulfate, or hyaluronic acid, or any combination thereof. According to exemplary embodiments of the present invention, the outer collagen tube with the internal matrix described above forms a conduit that forms a surprisingly synergistic microenvironment that enhances Schwann cell survival.

According to exemplary embodiments of the present invention, the slurry is subject to axial freezing. A cooling gradient is generated in the axial direction of the slurry when in the mold by rapid heat transfer from the slurry to a cooling medium, and where the cooling gradient has substantially no radial component. Cooling in this manner forms substantially parallel, axially aligned ice crystals in the slurry. According to certain exemplary embodiments, a heat sink at one end of the slurry causes heat to be drawn out of the slurry in an axial manner. A heat sink in accordance with the principles of the present invention includes a thermally conducting plug that contacts the slurry and in turn is in contact with a cooling medium. The thermally conducting plug acts as a heat sink, as well as sealing off one end of the tube where slurry is added to the tube. The plug can be made of any material that has high thermal conductivity, such as metals and metal alloys (e.g., brass, steel, copper, zinc, nickel, and aluminum, among others). The thermally conducting plug can be inserted into the mold that contains the slurry, thereby contacting the slurry. According to one embodiment, the thermally conducting plug can serve as a stop within the mold, such as when the mold shape is a cylinder and is positioned perpendicular to the cooling medium with the thermally conducting plug directly contacting the cooling medium. According to another exemplary embodiment, the slurry that is used to fill the hollow outer collagen tube or conduit is frozen along an axial direction of the slurry, with the slurry having no detectable radial thermal gradient, to form a frozen slurry having parallel axially aligned crystals. According to another exemplary embodiment, the step of freezing includes contacting the proximal end of the outer collagen tube or conduit to a heat sink with the slurry freezing from a proximal end of the slurry to a distal end of the slurry to form the frozen so that a slurry cooling gradient is generated in the axial direction of the slurry when in the mold by rapid heat transfer from the slurry to a cooling medium, and where the cooling gradient has substantially no radial component.

Suitable cooling media include any solid or liquid media capable of freezing the liquid slurry, for example, a cooling medium that maintains a temperature between about −78° C. and about −196° C. Certain exemplary embodiments of the method of the invention include the step of contacting the thermally conducting plug with a cooling medium to provide a cooling gradient in the axial direction of the insulated tube. The cooling medium may be at least one of liquid nitrogen, dry ice, an isopropanol/dry ice mixture, and silicone oil cooled by liquid nitrogen, and the like, whether directly contacting the thermally conducting plug or indirectly through a different media such as a cold plate and the like. The cooling media can be used alone or in combination with each other. It is to be understood that the list of cooling media is not exhaustive and that one of skill in the art will readily identify other cooling media useful to freeze slurries based on the present disclosure. Once the slurry, such as an aqueous slurry, is completely frozen, the tube filled with frozen aqueous slurry is dried under vacuum (e.g., by freeze drying or lyophilizing) to produce a nerve regeneration conduit of the present invention.

As heat is drawn out of the slurry in an axial manner by the heat sink, freezing of the slurry proceeds along the length of the slurry from the end of the slurry proximal to the heat sink to the distal end of the slurry. The slurry, whether directly in a mold or in a conduit, is thermally insulated with little or no significant thermal gradient to significantly affect freezing of the slurry at the point of contact of the slurry with the wall of the mold or the conduit.

Axial freezing combined with thermal insulation followed by freeze drying produces substantially parallel, axially aligned pores extending the length of the matrix. Ice crystal formation occurs along the gradient of cooling. If the temperature gradient is uniform through a volume of space, and each plane in the volume perpendicular to the direction of the temperature gradient is of a uniform temperature, and the gradient is sufficient to propagate ice crystal formation throughout the length of the gradient, then the formation of ice crystals in such a defined region will extend through the region in a manner aligned to the direction of the gradient. Thus, the ice crystals will be substantially parallel to the gradient and substantially parallel to each other. In certain exemplary embodiments of an aqueous slurry and a tubular mold, this axial cooling gradient is achieved by thermally insulating the aqueous slurry or the walls of the tube containing the aqueous slurry to be frozen. Insulating the tube can be done with any material that prevents heat transfer through the wall of the tube. This substantially eliminates any radial component in the cooling gradient, providing a uniform axial cooling gradient. Subsequent freeze drying or lyophilizing of the frozen slurry in the tube results in a matrix having open channels comprising substantially parallel, axially oriented pores.

According to another exemplary embodiment of the present invention, the outer collagen tube and the slurry used to fill the tube are subject to direct freeze-drying. The collagen tube and the slurry are direct freeze-dried along an axial direction of the slurry. According to another exemplary embodiment, the slurry has no detectable radial thermal gradient during direct freeze-drying and forms a frozen slurry having parallel axially aligned crystals. According to another exemplary embodiment, the direct freeze-drying of the collagen tube and the slurry removes the parallel axially aligned crystals and forms the internal matrix that has parallel axially aligned outer tube/conduit pores and internal matrix pores that span one end of the matrix to the other. Accordingly, the direct freeze-drying of the outer collagen tube with the internal matrix forms a conduit that forms a microenvironment that enhances Schwann cell survival.

The pores of the matrix, internal matrix, and the outer tube or conduit have an average diameter of about 10 μm to about 300 μm, about 50 μm to about 250 μm, about 75 μm to about 200 μm, 50 μm to about 150 μm, 50 μm to about 80 μm, about 100 μm to about 200 μm, or about 50 μm to about 250 μm. According to another exemplary embodiment, the pores have an average diameter of about 5 μm to about 360 μm or about 160 μm to about 180 μm. The matrix can be any length depending upon the desired application, however, suitable lengths include from about 2 cm to about 20 cm, from about 3 cm to about 15 cm or from about 5 cm to about 10 cm and ranges therebetween.

In certain exemplary embodiments, the resorbable tube/outer tube or conduit has an abluminal surface with an irregular surface pore structure. The pores of the abluminal surface have an average diameter of about 20 μm to about 200 μm, about 40 μm to about 180 μm, about 60 μm to about 160 μm, 80 μm to about 140 μm, 100 μm to about 120 μm, about 100 μm to about 200 μm, or about 50 μm to about 150 μm.

In accordance with a certain aspect of the invention, the matrix of the present invention is used to promote in vivo regeneration of a severed mammalian nerve so as to bridge a gap between a first end and a second end of the severed nerve. The matrix can be included within a conduit having a first end and a second end. The matrix may be flush with the first end and second end of the conduit or it may be recessed within one or both ends of the conduit. Alternatively, the matrix may extend beyond one or both ends of the conduit, if desired. According to one embodiment, connectors may be used to connect the conduit containing the matrix, or the matrix alone, to the severed end of a nerve. Suitable connectors within the scope of the present invention overlap the conduit and the nerve and include wraps or cuffs with or without sutures or any other suitable connector design that can be used to connect the conduit or matrix to the severed end of a nerve.

One particular example of a connector is a collagen sheet or wrap that can be placed or wrapped around the nerve and the conduit and then secured in place, such as by using sutures. One such collagen sheet or wrap is marketed under the NEURAWRAP mark from Integra LifeSciences Corporation, Plainsboro, N.J. Such sheets or wraps can be in a cylindrical form having a longitudinal slit where opposing ends of the wrap can be pulled apart, the nerve inserted and then the wrap can rebound into a cylindrical position around the nerve. Such sheets or wraps can be made from biodegradable or bioerodable materials such as collagen, laminin, fibronectin, merosin, hyaluronic acid, chitin, chitosan, keratin, polyglycolic acid, polylactic acid, cellulose and the like. The materials can be used alone or in combination with each other. It is to be understood that the list of materials is not exhaustive and that one of skill in the art will readily identify other materials useful to make sheets or wraps based on the present disclosure.

Where the matrix is flush with an end of the conduit, another suitable connector is a cuff having a first open end and a second open end. The cuff has an outer diameter larger than the outer diameter of the conduit. The cuff conforms to the outer shape of the conduit. For example, if the conduit is tubular or cylindrical, the cuff will be a tubular or cylindrical cuff. A cuff is placed onto the outer end of the conduit with a portion of the cuff extending over the end of the conduit. The first end of the severed nerve is inserted into the cuff extension and is brought into contact with the first end of the matrix to form a first junction between the severed nerve and the conduit. The nerve, cuff and conduit are all secured in place at this first junction according to methods known to those skilled in the art, such as suturing. The second end of the severed nerve is brought into contact with the second end of the matrix to form a second junction between the severed nerve and the conduit. This junction may also be secured in place with a cuff as described above. Cuffs according to embodiments of the present invention can be formed from various materials including collagen laminin, fibronectin, merosin, hyaluronic acid, chitin, chitosan, keratin, polyglycolic acid, polylactic acid, cellulose and the like. The materials can be used alone or in combination with each other. It is to be understood that the list of materials is not exhaustive and that one of skill in the art will readily identify other materials useful to make cuffs based on the present disclosure. Suitable commercially available cuffs include resorbable collagen tubes having a length sufficient for a cuff, as are commercially available under the brand name NEURAGEN from Integra LifeSciences Corporation, Plainsboro, N.J. Methods for making certain exemplary embodiments of the resorbable tube are disclosed in U.S. Pat. No. 5,019,087, which is incorporated herein by reference in its entirety.

If, according to an exemplary embodiment, the matrix is recessed within one or both ends of the conduit, i.e. the end of the conduit extends past the matrix therein, the severed nerve is introduced into the conduct until it contacts the matrix to form a junction and the nerve is secured in place within the conduit using methods known to those skilled in the art, such as suturing. No connector such as a sheet, wrap or cuff is required with this exemplary embodiment, although a sheet, wrap or cuff could still be used if desired.

In certain exemplary embodiments where the ends of the conduit, such as a resorbable tube, extend past matrix therein, a distance into each end of the tube is unfilled with the slurry to form the matrix, or alternatively, matrix is removed from within the tube, or still alternatively, matrix of length shorter than the tube is inserted into the tube. Methods for making an embodiment where the matrix is formed within the tube include plugging the bottom of the tube with a plug that extends a distance into the tube, followed by filling the tube with slurry up to a desired point, which can include the end of the tube or a location before the end of the tube thereby allowing the end of the tube to extend past the matrix. These embodiments allow insertion of a severed nerve end into a hollow end of the resorbable tube and contact of the nerve end with the matrix inside the tube. The nerve end inside the hollow end of the resorbable tube may then be sutured to the tube.

In a certain exemplary embodiment, nerve regeneration conduits according to the present invention include a resorbable tube having a matrix of controlled pore size and parallel structure that mimics Schwann cell basal lamina, which significantly enhances Schwann cell migration and axon regeneration through the conduit. Schwann cells are non-neuronal cellular elements that provide structural support and insulation to axons. Thus, by using the conduits of the present invention in a manner such that the respective ends of a severed nerve are brought into contact with each end of the conduit fashioned from a resorbable tube filled with a matrix having substantially parallel, axially aligned pores extending the length of the matrix, greater numbers of regenerating axons are stimulated, many of which become mylenated, a substantial increase in the initial rate of the outgrowth of fibers and mylenated axons is produced, and the regenerating axons are able to span the gap between the severed nerve by growing through the matrix.

The matrices of the present invention promote parallel axial alignment of regenerated nerve tissue accompanied by a large number of Schwann cells. The axial oriented pores of the matrices of the present invention promote peripheral nerve regeneration that is axially aligned to the direction of the resorbable matrix, with the oriented pores being substantially parallel to each other along the entire length of the desired route of nerve regeneration. For example, an axon entering a pore of the nerve regeneration conduit of the present invention should exit the opposite end of the conduit at substantially the same relative position.

The pore size and parallel alignment in the matrix are intended to resemble the Schwann cell basal lamina so as to encourage axon growth. In certain exemplary embodiments, the population of pores in the matrix have an average diameter of about 10 μm to about 300 μm. In an alternate embodiment, the population of the pores in the matrix have an average diameter from about 40 μm to about 180 μm or an average diameter from about 80 μm to about 120 μm.

Certain exemplary embodiments of the present invention are directed to a system including an apparatus used to freeze the slurries of the present invention. The apparatus includes a vessel filled with a heat transfer fluid and including a coil through which coolant flows. The temperature of the fluid is monitored and controlled at a desired temperature. A collagen tube of desired size is fitted at one end with a heat sink such as a copper rod and the collagen tube is inserted into PVC tubing. The PVC tubing with the collagen tube and copper rod is housed in insulating material with the heat sink protruding beyond the insulating material. According to one method of the present invention, a slurry is poured into the collagen tube and the heat sink is contacted to the heat transfer fluid, i.e. liquid cooling medium, with the insulating material acting as a float, as the insulating material is buoyant when placed in the liquid cooling material. In this embodiment the collagen tube is held in a substantially vertical position within the insulating material with the heat sink contacting the liquid cooling material. The slurry is allowed to freeze and the frozen slurry is then lyophilized to form a matrix. The matrix may then be further processed such as by undergoing crosslinking. The matrix may then be packaged and sterilized according to methods known to those of skill in the art.

Certain other exemplary embodiments of the method of the present invention include surrounding a bioresorbable or biodegradable tube have a thermally conducting plug at one end with a material that thermally insulates the tube and the slurry within so that there is substantially no thermal gradient in the radial direction of the tube. As a non-limiting example, the tube may be inserted into a block of polymer foam, polystyrene block, or other insulating material, such as STYROFOAM or AEROGEL, so that the plug protrudes from the bottom of the block and the open end of the tube is flush with the top of the block. The block of polymer foam serves as a thermal insulator to prevent heat transfer through the walls of the tube. Thus, any thermal gradient in the tube will have substantially no radial component. The polymer foam may comprise one or more of the following insulating materials: polystyrene, polyurethane, polyethylene, ceramic and silicone, and the like. The insulating media can be used alone or in combination with each other. It is to be understood that the list of insulating media is not exhaustive and that one of skill in the art will readily identify other insulating media based on the present disclosure. Alternatively, the tube may be insulated with any other material that substantially prevents heat transfer, for example, a vacuum- or gas-filled jacket or flask.

In certain exemplary embodiments, the method of using matrices, especially matrix-filled conduits, includes the steps of bringing the respective ends of the severed nerve into contact with each end of the nerve regeneration conduit of the present invention, which conduit is equal to or longer than the gap to be bridged so that no tension is placed upon the severed nerve. Both the distal and proximal nerve ends are partially inserted into the ends of the resorbable tube, optionally until the nerve ends contact the matrix filling the tube, and sutured over their perineuerium.

Use of the nerve regeneration conduit of the present invention promotes nerve regeneration across nerve gaps of up to 15 cm. In certain exemplary embodiments, the nerve regeneration conduit promotes regeneration across nerve gaps of about 2 cm to about 10 cm, e.g., about 2 cm to about 4 cm, about 3 cm to about 7 cm. Nerve diameters that can be accommodated by the nerve regeneration conduit of the present invention range from about 1 mm to about 1.5 cm, e.g., about 2 mm and about 7 mm, about 3 mm to about 10 mm.

EXAMPLES

The following examples are specific embodiments of the present invention but are not intended to limit it.

Example 1

A resorbable tube having a porous matrix according to the present invention was achieved by highly controlled freezing and insulation of an aqueous dispersion of collagen, followed by freeze drying. The pore structure and orientation of the matrix formed by the process of the invention was examined by taking scanning electron microscope (SEM) images of transverse and longitudinal cross-sections of the resulting matrix.

Specifically, a brass bolt was inserted into one end of a NEUROGEN collagen tube to both plug the tube and act as a heat sink. The tube was then inserted into a polystyrene foam block so that the bolt protruded from the bottom face of the block, and the open end of the tube was flush with the top face of the block. An aqueous collagen slurry was prepared according to the method described in U.S. Pat. No. 6,969,523 hereby incorporated by reference herein in its entirety. Suitable methods to prepare a slurry useful in the present invention are also described in U.S. Pat. No. 5,997,895 hereby incorporated herein by reference in its entirety. The tube was filled with the aqueous collagen slurry, and the polystyrene foam block was floated with the bolt on the bottom face of the block immersed in a bath of silicone oil that had been cooled by liquid nitrogen. The collagen slurry in the tube froze entirely within about 30 minutes. The tube with the frozen slurry was then placed in a pre-cooled lyophilizer and freeze dried under vacuum.

Figure 2:
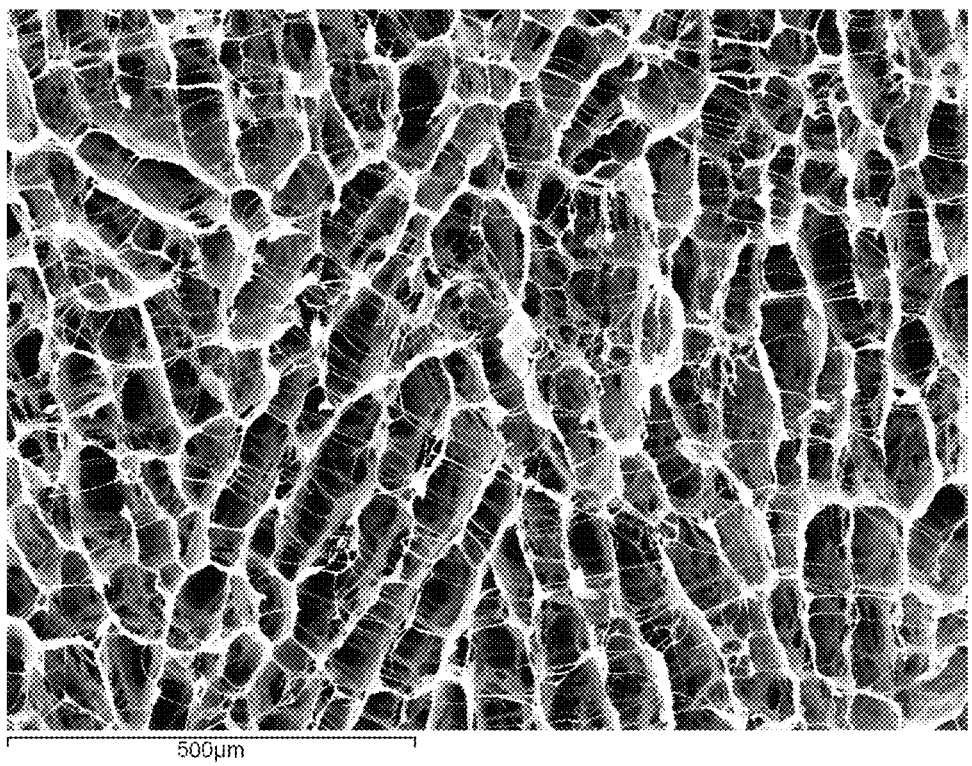
FIG. 2 is a scanning electron micrograph at 100× of a cross-section of a matrix produced by the method of the present invention.
Figure 3:
FIG. 3 is a scanning electron micrograph at 150× of a longitudinal cross section of a matrix produced by the method of the present invention.

FIG. 1 is a scanning electron micrograph at 15× of a cross-section of a matrix produced by the method of the present invention. FIG. 2 shows the matrix at 100×. FIG. 3 is a scanning electron micrograph at 150× of a longitudinal cross section of a matrix produced by the method of the present invention.

FIG. 1-FIG. 3 show substantially uniform pore structures where the pores are substantially parallel, axially aligned, and extending the length of the matrix. The pores are believed to mimic the highly axially oriented pore structure of Schwann cell basal lamina.

Example 2

A 4.5 cm long by 7 mm diameter tube was provided having walls formed from collagen and a laminin-containing material according to the process of U.S. Pat. No. 5,019,087. A copper rod was inserted into one end of the tube to both plug the tube and act as a heat sink. The tube was then inserted into a polystyrene foam block so that the copper rod protruded from the bottom face of the block, and the open end of the tube was flush with the top face of the block. The tube was filled with aqueous slurry of collagen and a glycosaminoglycan, and the polystyrene foam block was floated with the copper rod on the bottom face of the block immersed in a bath of liquid nitrogen. The collagen slurry in the tube froze entirely within 12 minutes. The tube with the frozen slurry was then placed in a pre-cooled lyophilizer and freeze dried under vacuum. The resulting porous matrix inside the tube was examined in both cross-section and longitudinal section which showed a matrix having substantially parallel, axially oriented pores extending the length of the matrix. Average pore diameter was between about 165 µm to about 180 µm. The openness of the parallel pores was tested by inducing charged fluorescent beads to migrate through the porous matrix under the influence of a voltage gradient. The majority of the charged fluorescent beads were able to pass through the porous matrix from one end to the other, thus demonstrating that the majority of the parallel, axially aligned pores were open and extended along the length of the matrix.

Example 3

A tube was provided having walls formed from collagen and a laminin-containing material according to the process of U.S. Pat. No. 5,019,087. A copper rod was inserted into one end of the tube to both plug the tube and act as a heat sink. The tube was then inserted into a polystyrene foam block so that the copper rod protruded from the bottom face of the block, and the open end of the tube was flush with the top face of the block. The tube was filled with an aqueous slurry of collagen and a glycosaminoglycan made according to the method described in Example 1, and the polystyrene foam block was placed in a Styrofoam box partially-filled with dry ice so that the copper rod directly contacted the dry ice. The collagen slurry in the tube froze entirely within 1 hour 30 minutes. The tube with the frozen slurry was then placed in a pre-cooled lyophilizer and freeze dried under vacuum. The resulting porous matrix inside the tube was examined in both cross-section and longitudinal section which showed a matrix having substantially parallel, axially oriented pores extending the length of the matrix. Average pore diameter was about 361 µm. The average pore diameter resulting from the freezing method of this Example is notably larger than the average pore size resulting from the freezing method of Example 2, as it is believed that a slower freezing time allows for growth of larger ice crystals, which results in larger pores.

Example 4

An average freezing point of −22.03° C. was experimentally determined for an aqueous slurry of collagen and glycosaminoglycan by freezing five samples according to the table below.

| Sample | Weight (mg) | Freezing Temperature (°C.) |
| --- | --- | --- |
| 1 | 15.0 | −15.95 |
| 2 | 21.3 | −24.04 |
| 3 | 33.1 | −24.14 |
| 4 | 31.4 | −24.07 |
| 5 | 22.6 | −21.94 |

Example 5

Conduit Lab-scale Production. The conduit is composed of a hollow collagen tube and an internal matrix. The collagen conduit, or outer hollow tube, is composed of alkali-treated (AT) collagen. The collagen is stored at −20 C. The hollow collagen conduit is produced by making a slurry in the following manner. Cut small pieces from the frozen block of collagen and weigh out 1.18 g into a glass bottle. Prepare 0.5M lactic acid in distilled water at store at room temperature. Place the AT collagen into 100 ml lactic acid (0.5M). Leave the collagen to dissolve in lactic acid overnight at 4° C. The following day, prepare the large blender and a box full of ice. Pour the AT collagen into a beaker and place on the box of ice. Blend at 15,000 rpm and monitor how well the collagen is dispersing. This should be completely dispersed in about 10-15 minutes. Make sure that the collagen is always cool to avoid denaturation. Use a vacuum filter that has been modified with 100 and 200 mesh. Use the 100 mesh first the filter the slurry. Once the slurry has passed through, repeat the same thing with the 200 mesh. Store the slurry at 4° C.

Prepare mandrels using stainless steel rods and PTFE tape. Use the tape to wrap around the stainless steel rods with enough tape to create the desired diameter (1.5/3/5 mm). Measure the mandrels with vernier callipers to ensure the desired diameter has been created. Clean the mandrels as well as the glass/plastic vials for spinning the collagen using 0.05M acetic acid. Prepare 2.5M NaOH. Prepare 0.3% formaldehyde. Set up the dental drill and ensure that the speed is set to approximately 7.5. Attach the mandrels onto the dental drill. Place 10 ml of slurry into a vial. Add approximately 1.5-1.6 ml NaOH (2.5M) into the slurry—add a few drops at a time. Shake vigorously or use a vortex making sure that the top is covered. The slurry should turn cloudy soon after which will indicate that the collagen has precipitated. Make sure that the precipitation is homogenously distributed. Check to pH and ensure that it is between 5.4 and 6. This volume should be enough to make a conduit of 1.5 mm internal diameter, 5 cm in length. The ends of the conduit may have to be trimmed off. Place the mandrel attached to the drill into the vial containing the precipitated collagen. Spin the mandrel and make sure that the collagen is adhering onto the mandrel—do this for approximately 10 seconds. Subsequently, spin the mandrel on the inner edge of the vial so that the collagen is compressed onto the mandrel—do this for a further 10-20 seconds. The vial should now contain a clear suspension with no collagen visible.

Remove the mandrel from the vial and use the glass plates to compress the collagen further. Make sure that a glass spacer is between the glass plates. Place the mandrel between the glass plates making sure that the bottom end of the mandrel sits on the glass spacer so that the collagen does not spin out of the mandrel. Spin the mandrel at the same speed—7.5, for approximately 30 seconds. Detach the mandrel from the dental drill and place into falcon tubes containing 0.3% formaldehyde to cross-link the conduit for 90 minutes at room temperature. Subsequently, replace the formaldehyde with $dH_2O$ and wash 3 times. Place the mandrel into the dental drill again and spin between the glass plates to compress the collagen further for approximately 20 seconds. Subsequently, place the mandrels in a freezer at −20° C. making sure that they are spaced well from each other. Leave the mandrels in the freezer overnight. The following day, place the mandrels containing the collagen on a stainless steel tray and freeze-dry at a final temperature of −40° C. Once the collagen has been freeze-dried, carefully remove them from the mandrels making sure not cause tears on the collagen. This can be done by spraying the collagen with 100% ethanol, then remove excess ethanol by placing the mandrels on kimwipes/tissue. This should allow the collagen conduits to easily slide out of the mandrels with little damage caused. Allow the conduits to air dry overnight at room temperature.

Example 6

Internal matrix slurry production. The internal matrix is made from a slurry of 0.5% microfibrillar collagen, 0.044% chondroitin sulfate (from shark cartilage). Prepare 0.05M glacial acetic acid Weigh 0.6 g microfibrillar collagen and place in a beaker containing 100 ml acetic acid (0.05M). Weigh 0.053 g chondroitin sulfate and place in a beaker containing 20 ml acetic acid (0.05M). Leave the collagen and chondroitin sulfate in the fridge at 4 C overnight to dissolve. The following day, place the collagen in a box of ice and blend (15,000 rpm) initially for approximately 30 minutes and then slowly add the chondroitin sulfate using a syringe and tubing, a few milliliters at a time while blending. Blend for a further 10 minutes and subsequently de-gas to remove the air from the slurry. Place the slurry in a fridge at 4 C until needed but ensure that it is de-gassed again before using.

For the incorporation of macromolecules (fibronectin and/or laminin-1/-2) directly into the suspension, the desired concentration (initially chosen as 25 µg/ml) was made in a solution of PBS and subsequently incorporated into the slurry. The slurry was then mixed with a magnetic stirrer for 30 minutes and subsequently de-gassed as before. Soak-loading could also be utilized as a method of incorporation by soaking a suspension of the macromolecules onto the internal matrix of a freeze-dried conduit using a syringe. This was done for approximately 1 hour at room temperature before re-freeze-drying at −40° C. final temperature.

Example 7

Filled conduit production. The filled conduit is produced using a 2-step process. The conduits are filled with the internal matrix slurry and then frozen using dry ice. The frozen conduits are then freeze-dried and cross-linked to produce the final product. Make sure that the internal matrix slurry is fully de-gassed. Place a hollow conduit into PTFE tubing with a stainless steel screw (heat sink) attached on one end. Allow approximately 5 mm of space between the conduit and stainless steel screw. Add the slurry into the PTFE tubing containing the conduit with a syringe and needle and allow the conduit to stand at room temperature for approximately 30 minutes. Subsequently, add more slurry into the conduit making sure to eliminate all air bubbles from the PTFE tubing using the syringe and needle. Place the PTFE tubing containing the conduit into a polystyrene block with a hole of the same diameter as the tubing. Make sure that the stainless steel screw protrudes out of the polystyrene block and the open end of the tubing does not protrude out i.e. make sure that the tubing is fully covered in the polystyrene.

The freezing process should be done in a flow-hood. Using thermo-insulating gloves, place dry ice into a polystyrene box (approx. 2 liters in volume). Pour isopropanol carefully into the dry ice. This should bubble up so make sure that a safety face mask is utilized. Place the polystyrene block containing the tubing with the conduit onto the dry ice and allow it to float making sure that the stainless steel screws are fully submerged in the isopropanol. The internal matrix within the conduit should freeze fully within 45 minutes if the polystyrene block is offers good insulation. Use an infra-red thermometer to ensure that the internal matrix has frozen (to below −20° C.) before removing the polystyrene block from the dry ice. Make sure not to interrupt the polystyrene block through movement so as to permit optimal directional freezing. Once frozen, remove the PTFE tubing from the polystyrene block and place in a box for storage at −80° C. overnight or until one is ready to freeze-dry. Pre-cool the freeze-drier to −40° C. under a vacuum of approximately 300 Torr. When the shelves reach the desired −40 C, release the vacuum and quickly open the freeze-drier and place the PTFE tubing containing the conduit and internal matrix on a stainless steel tray and onto one of the shelves. Freeze-dry to a final temperature of −40° C. and sublimate at 0° C.

Figure 4:
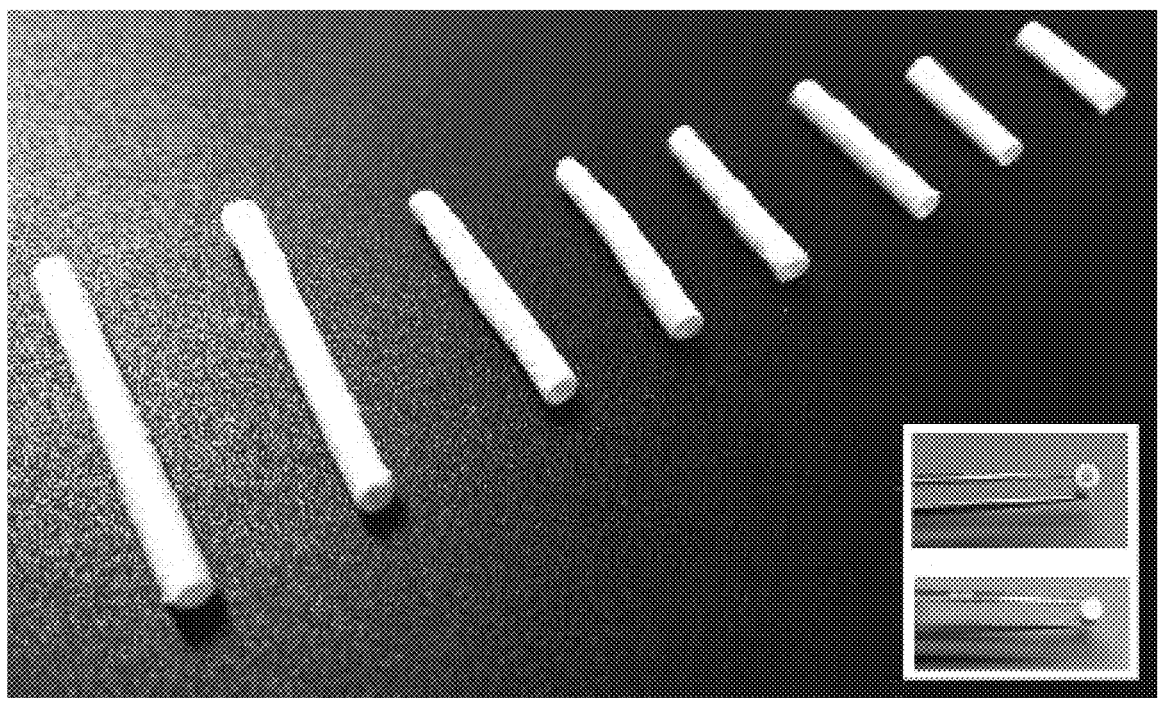
FIG. 4 is an image showing various sizes of prototype conduits fabricated, including hollow and filled conduits/collagen tubes.
Figure 5A:
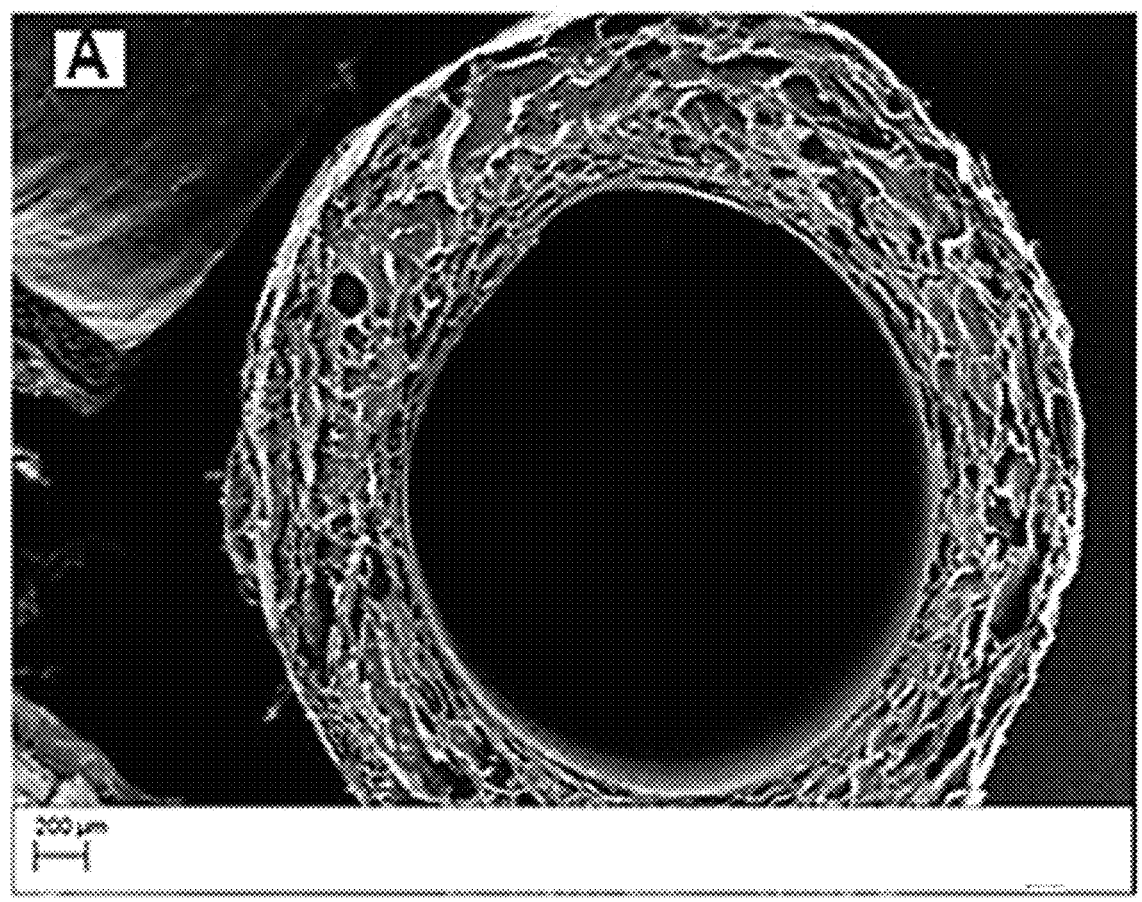
FIGS. 5A-D are scanning electron micrograph images of the hollow conduit/collagen tube. The cross-section shown in FIG. 5A highlights the pore structure of the conduit. The abluminal surface shown in FIGS. 5B and 5C has pore structures which are very irregular whereas the luminal surface, seen on the right side of the last image, FIG. 5D, has no pores detectable.
Figure 5B:
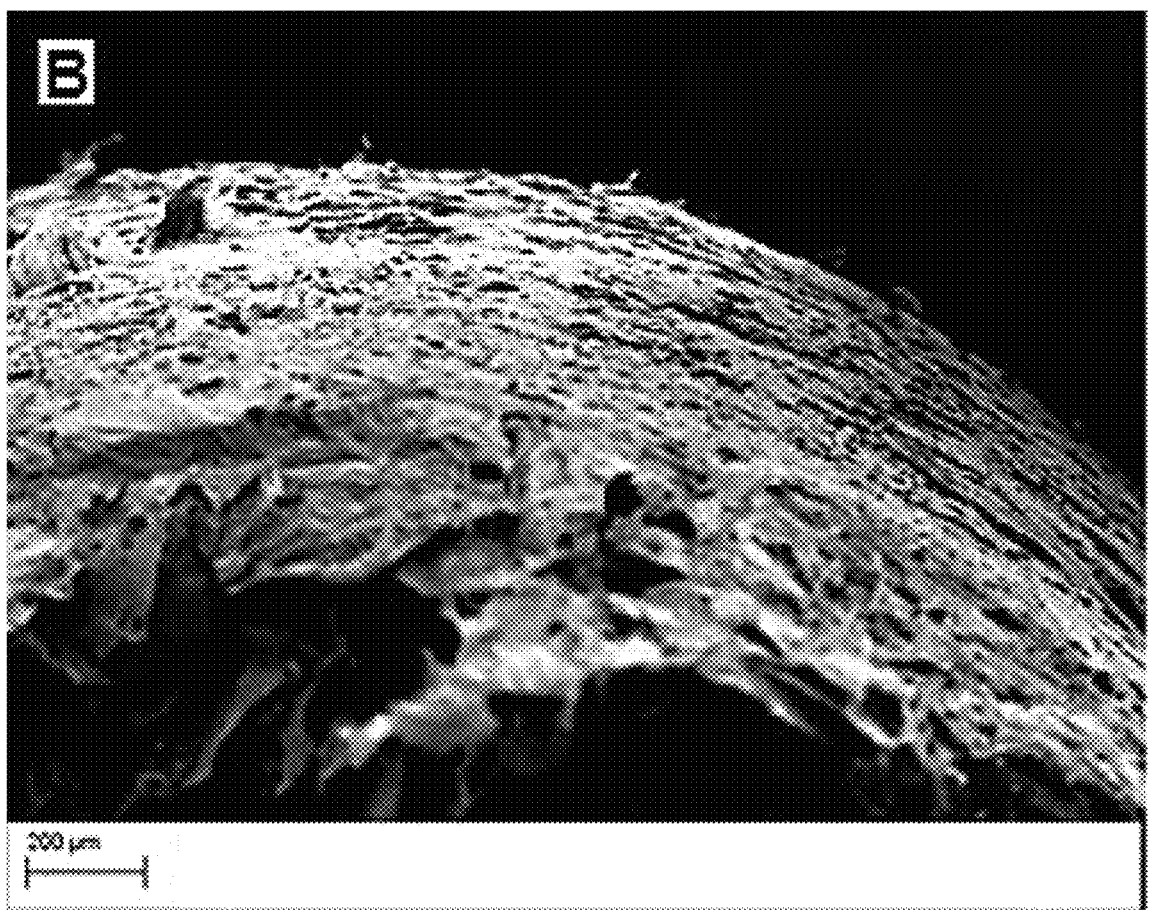
Figure 5C:
Figure 5D:
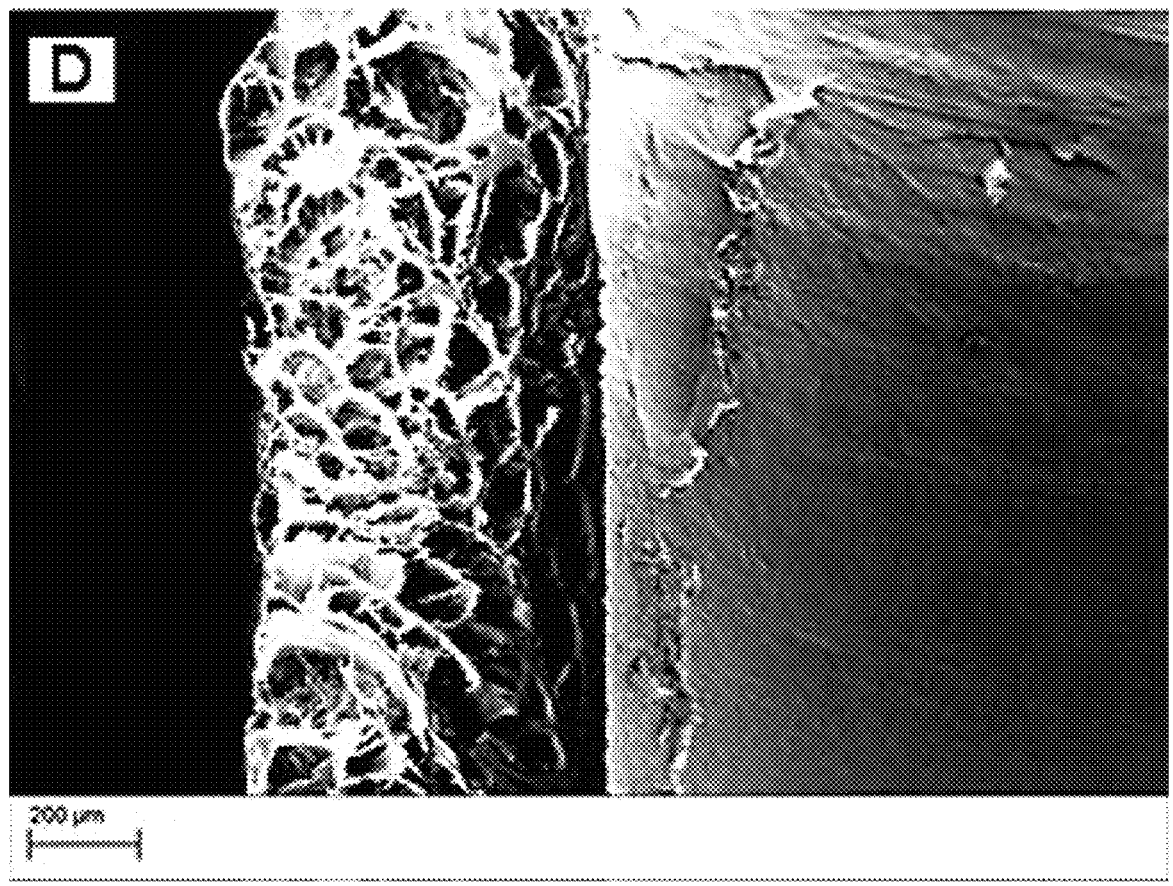
Figure 6A:
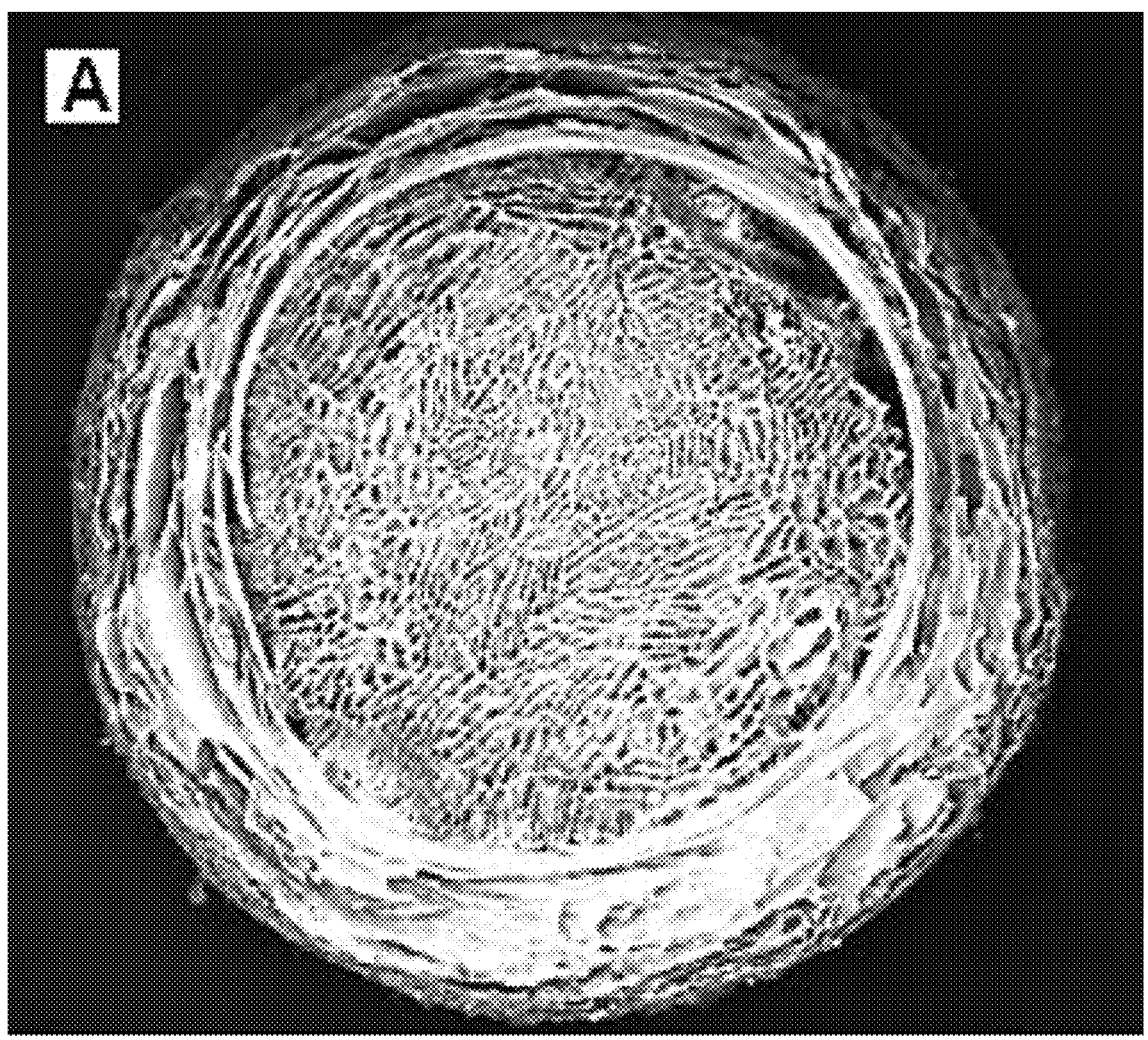
FIGS. 6A-D are scanning electron micrograph images of the filled conduit produced by the isopropanol freezing method. The cross-sections, FIGS. 6A and 6B, and longitudinal-sections, FIGS. 6C and 6D, demonstrate the interaction between the pore structure of the outer conduit/collagen tube and internal matrix.
Figure 6B:
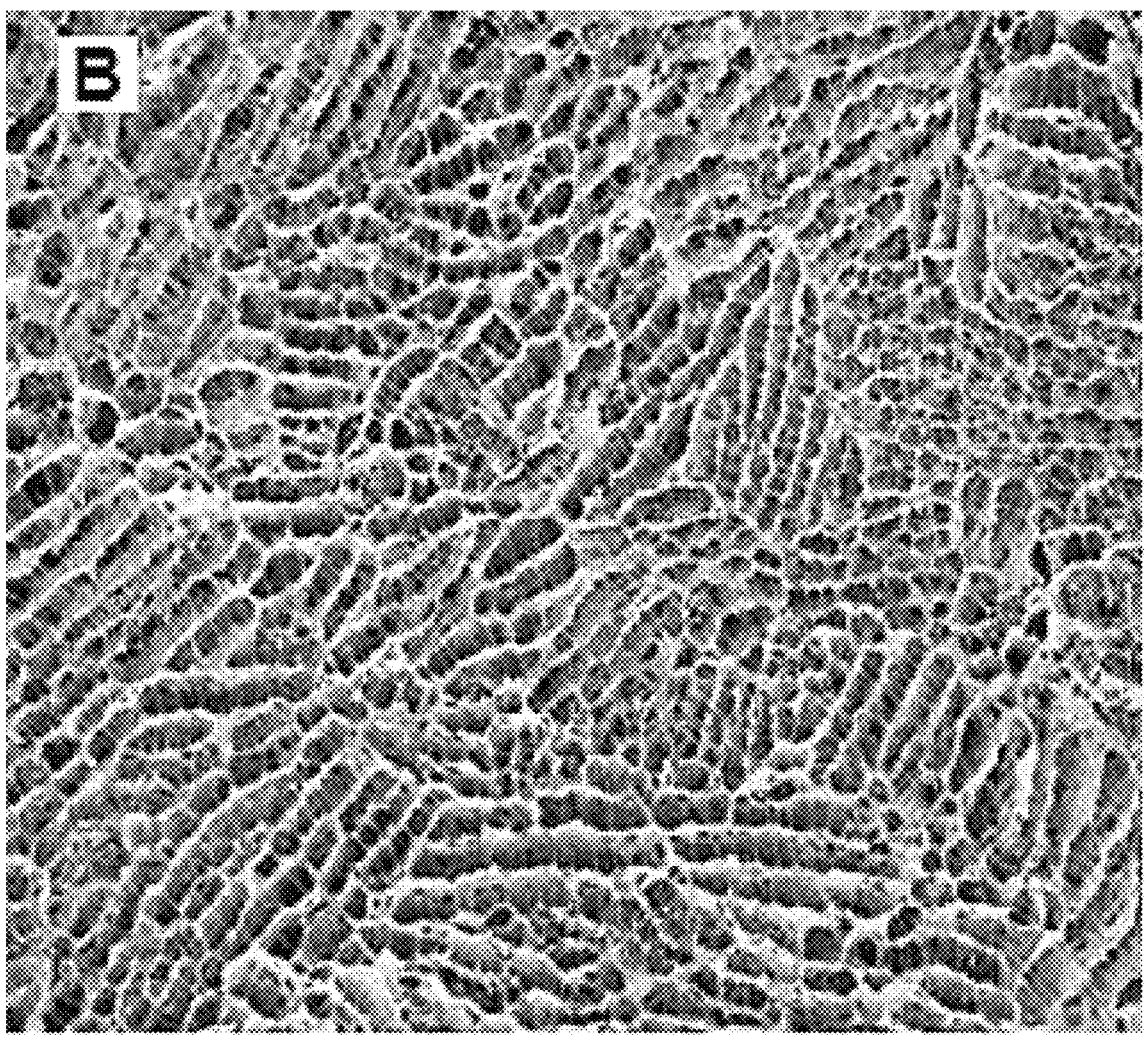
Figure 6C:
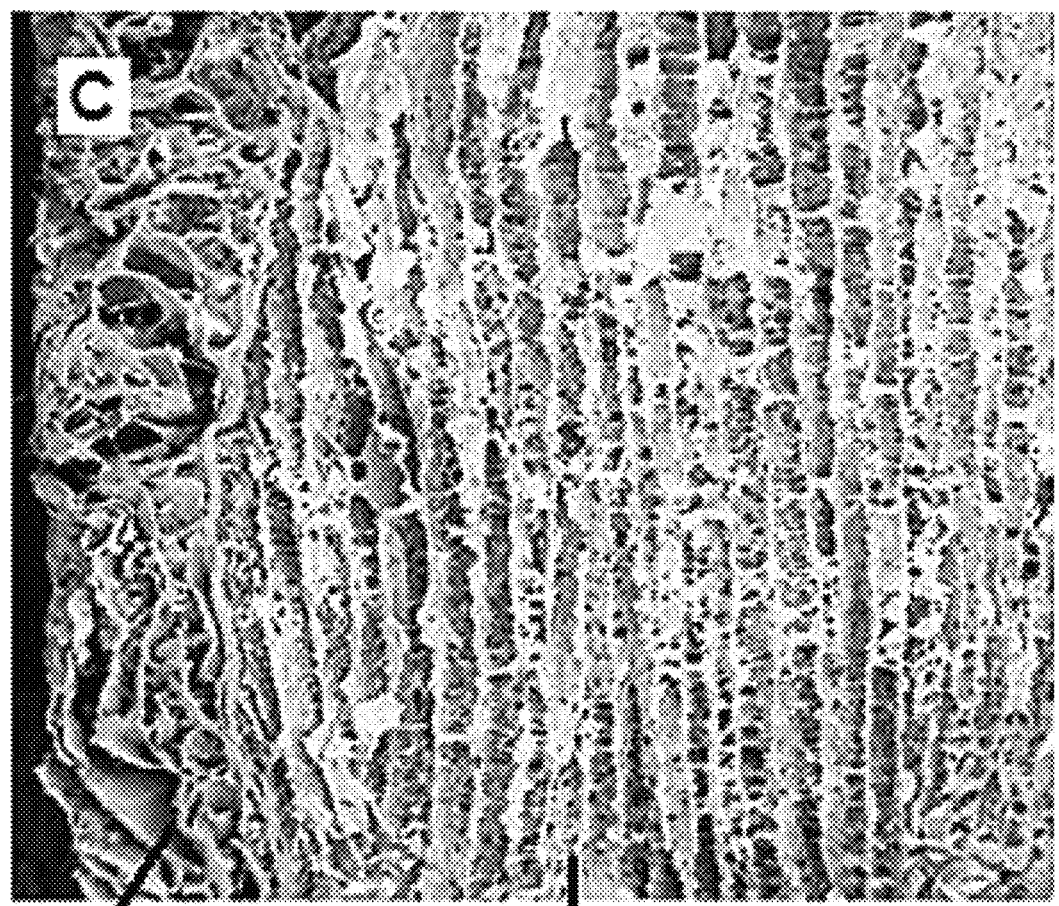
Figure 6D:

Subsequently, remove the conduits from the PTFE tubing carefully using dry forceps. See FIG. 4. Place the filled conduits in the vacuum oven at 105° C. for 24 hours to sterilize and cross-link. For long-term studies, cross-link the filled conduits in sterile 0.3% formaldehyde and subsequently wash 3 times with dH$_2$O.

Example 8

Figure 16:
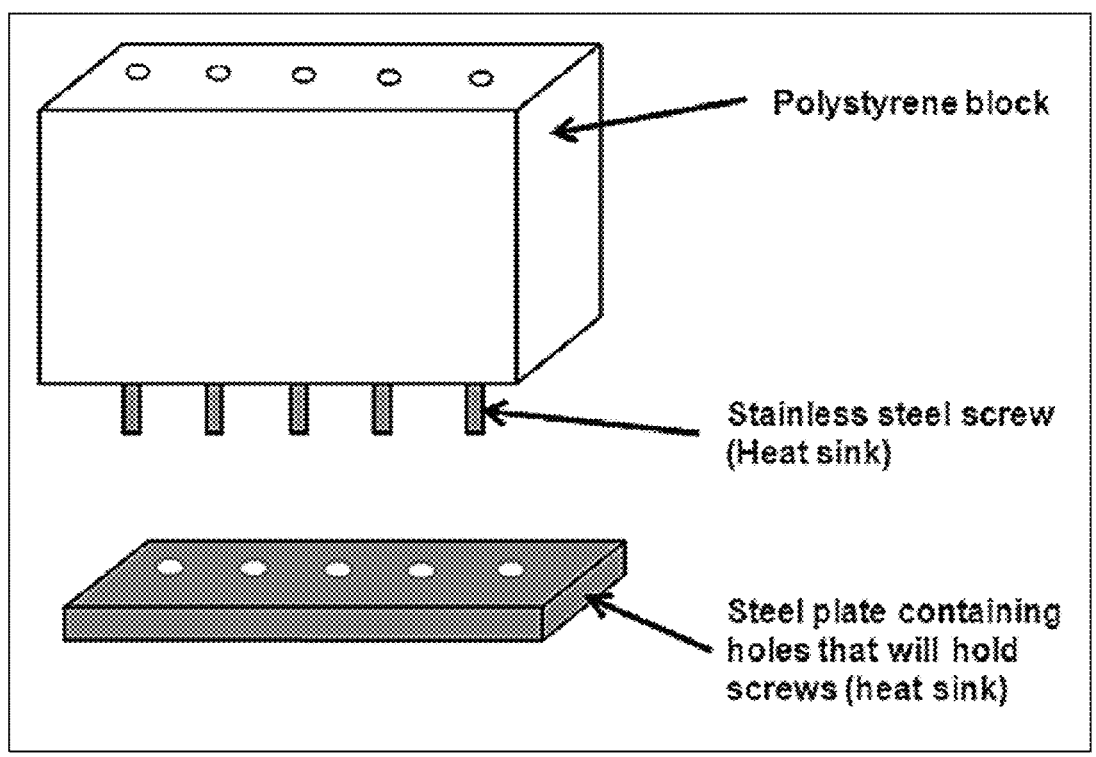
FIG. 16 depicts a potential set up for a direct freeze-drying method. The system includes a polystyrene block with multiple molds, stainless steel screws, or other thermally conducting plug, pole, etc.

Direct freeze drying. This method was developed to eliminate the multiple steps required for the fabrication of the filled conduit. As before, the conduit was placed into the PTFE tubing and filled with the slurry of the internal matrix. The tubing was also placed into the polystyrene block as before but rather than freezing with dry ice, the polystyrene block was placed directly onto the shelf of the freeze-dryer. Set up the freeze-dryer so that the cooling rate is 1° C./min to a final temperature of −40° C. Sublimate the sample at 0° C. for 17 hours. This method will only work if the slurry is de-gassed thoroughly. The stainless steel screws must also have good contact with the freeze-dryer shelf. This could be solved by using a stainless steel tray filled with water so that the screws are submerged in the water. A mold was designed and can be used to simplify the process further. See FIG. 16.

Example 9

The mechanical assessment of the conduit was carried out using suture pull-out tests and cyclic compression tests. Morphological assessment of conduit structure and pore sizes was based on analyzing SEM images. The methods used for these tests are described below.

This assessment was carried out to elucidate the ability of the conduits to hold a suture under loads exceeding those anticipated in the intended use environment and therefore determine the strength of the conduit with respect to the break strength of a suture. Nylon sutures of sizes 10-0/9-0/8-0/7-0/6-0 were obtained for the assessment of suture pull-out strength. A 10 mm conduit was hydrated for 1 hour in PBS at room temperature. One end of the conduit (2-5 mm from the end) was then firmly held by a specimen clamp attached to the bottom platen of the Zwick testing machine. A suture (10-0/9-0/8-0/7-0/6-0) was then passed through the other end of the conduit (1 mm or 2 mm from the end) and tied to the top platen of the Zwick testing machine. The machine was set up so that the cross-head speed was 2.5 mm/min under tension. Samples were tested and the end point was determined as—when either the suture broke or the conduit tore apart. The suture breakage or conduit tear led to a decrease in force which automatically stopped the machine from recording of resistance to tension. The table below outlines the suture pull-out test data.

| Suture Size 10-0 | Suture Break | Conduit Break | Force (N) | Suture Size 9-0 | Suture Break | Conduit Break | Force (N) |
|---|---|---|---|---|---|---|---|
| 1 | x | | 0.75 | 1 | x | | 0.95 |
| 2 | x | | 0.72 | 2 | x | | 0.91 |
| 3 | x | | 0.68 | 3 | x | | 0.97 |
| 4 | x | | 0.61 | 4 | x | | 0.89 |
| 5 | x | | 0.88 | 5 | x | | 0.84 |
| 6 | x | | 0.85 | 6 | x | | 1.02 |
| 7 | x | | 0.89 | 7 | x | | 1.1 |
| 8 | x | | 0.77 | 8 | x | | 0.94 |
| 9 | x | | 0.73 | 9 | x | | 0.93 |
| 10 | x | | 0.78 | 10 | x | | 0.96 |
| 11 | x | | 0.62 | 11 | x | | 1.07 |
| 12 | x | | 0.63 | 12 | x | | 0.98 |
| 13 | x | | 0.71 | 13 | x | | 1.04 |
| 14 | x | | 0.74 | 14 | x | | 1.02 |
| 15 | x | | 0.76 | 15 | x | | 0.94 |
| 16 | x | | 0.58 | 16 | x | | 1.15 |
| 17 | x | | 0.61 | 17 | x | | 1.08 |
| 18 | x | | 0.69 | 18 | x | | 1.17 |
| 19 | x | | 0.67 | 19 | x | | 1.09 |
| 20 | x | | 0.75 | 20 | x | | 1.11 |

| Suture Size 8-0 | Suture Break | Conduit Break | Force (N) | Suture Size 7-0 | Suture Break | Conduit Break | Force (N) |
|---|---|---|---|---|---|---|---|
| 1 | | x | 1.25 | 1 | | x | 1.56 |
| 2 | | x | 1.47 | 2 | | x | 1.62 |
| 3 | x | x | 1.31 | 3 | | x | 1.73 |
| 4 | x | | 1.14 | 4 | | x | 1.54 |
| 5 | | x | 1.56 | 5 | | x | 1.77 |
| 6 | | x | 1.49 | 6 | | x | 1.79 |
| 7 | x | | 1.38 | 7 | | x | 1.85 |
| 8 | x | x | 1.31 | 8 | | x | 1.51 |
| 9 | x | | 1.42 | 9 | | x | 1.89 |
| 10 | | x | 1.21 | 10 | | x | 1.95 |
| 11 | x | | 1.19 | 11 | | x | 1.85 |
| 12 | | x | 1.54 | 12 | | x | 1.72 |
| 13 | x | x | 1.43 | 13 | | x | 1.88 |
| 14 | x | x | 1.57 | 14 | | x | 1.66 |
| 15 | x | | 1.27 | 15 | | x | 1.92 |
| 16 | | x | 1.48 | 16 | | x | 1.78 |
| 17 | | x | 1.44 | 17 | | x | 1.74 |
| 18 | x | | 1.26 | 18 | | x | 1.48 |
| 19 | | x | 1.36 | 19 | | x | 1.67 |
| 20 | x | | 1.39 | 20 | | x | 1.78 |

| Suture Size 6-0 | Suture Break | Conduit Break | Force (N) |
|---|---|---|---|
| 1 | | x | 1.65 |
| 2 | | x | 1.79 |
| 3 | | x | 1.98 |
| 4 | | x | 1.63 |
| 5 | | x | 1.74 |
| 6 | | x | 1.71 |
| 7 | | x | 1.93 |
| 8 | | x | 2.04 |
| 9 | | x | 1.74 |
| 10 | | x | 2.06 |
| 11 | | x | 1.68 |
| 12 | | x | 1.89 |
| 13 | | x | 2.11 |
| 14 | | x | 2.04 |
| 15 | | x | 1.76 |
| 16 | | x | 1.88 |
| 17 | | x | 1.81 |
| 18 | | x | 1.70 |
| 19 | | x | 2.19 |
| 20 | | x | 1.96 |

The data collected from the suture pull-out tests showed that the conduit could resist tearing when sutures of sizes 10-0 and 9-0 were applied under tension. 8-0 sutures resulted in approximately 50% suture breakage or conduit tear signifying that this is the limit in suture size for the prototype conduits. 7-0 and 6-0 sutures both led to conduits tearing. The table below summarizes the data. "TEAR" signifies that the suture or conduit tore apart after a tensile load was applied. "X" signifies that the suture or conduit did not tear apart after a tensile load was applied. "TEAR/X" signifies that approximately 50% of conduits tore or sutures broke apart after a tensile load was applied.

| SUTURE SIZE (DIAMETER) | SUTURE | CONDUIT |
|---|---|---|
| 10-0 (0.02 mm) | TEAR | X |
| 9-0 (0.03 mm) | TEAR | X |

| SUTURE SIZE (DIAMETER) | SUTURE | CONDUIT |
|---|---|---|
| 8-0 (0.04 mm) | TEAR/X | TEAR/X |
| 7-0 (0.05 mm) | X | TEAR |
| 6-0 (0.07 mm) | X | TEAR |

Figure 8:
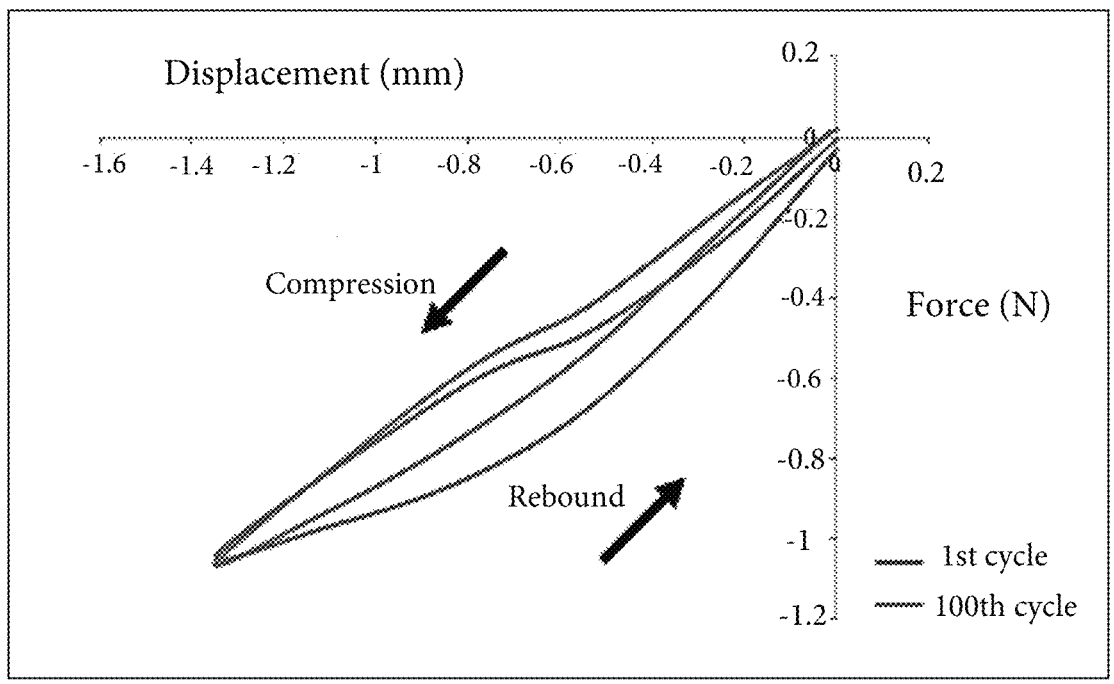
FIG. 8 is a graphical comparison of displacement vs. force of conduit under compressive load between the 1st cycle and 100th cycle.
Figure 9:
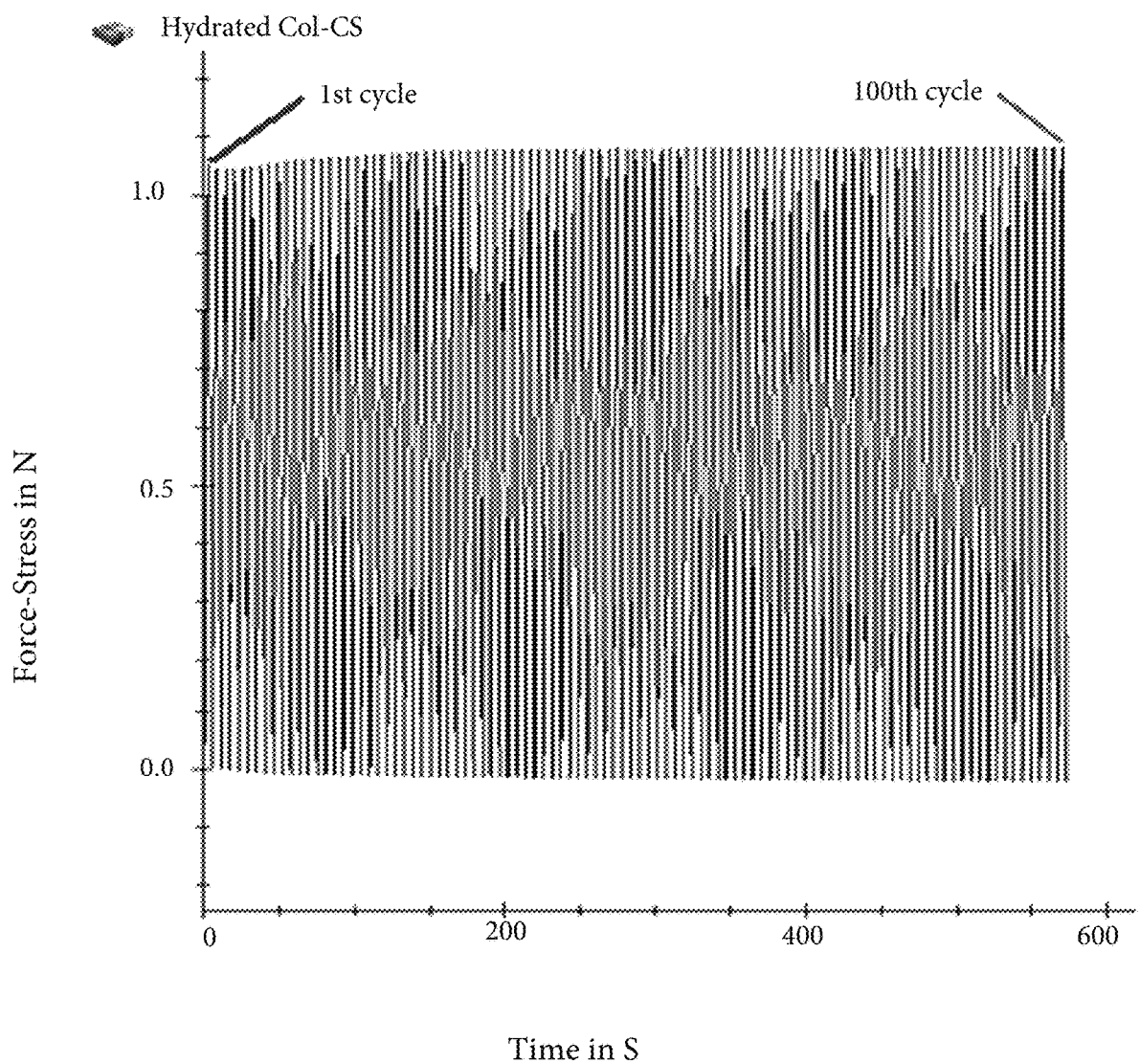
FIG. 9 is a graphically depicts typical stress vs time of a conduit under compressive load for 100 cycles.
Figure 10:
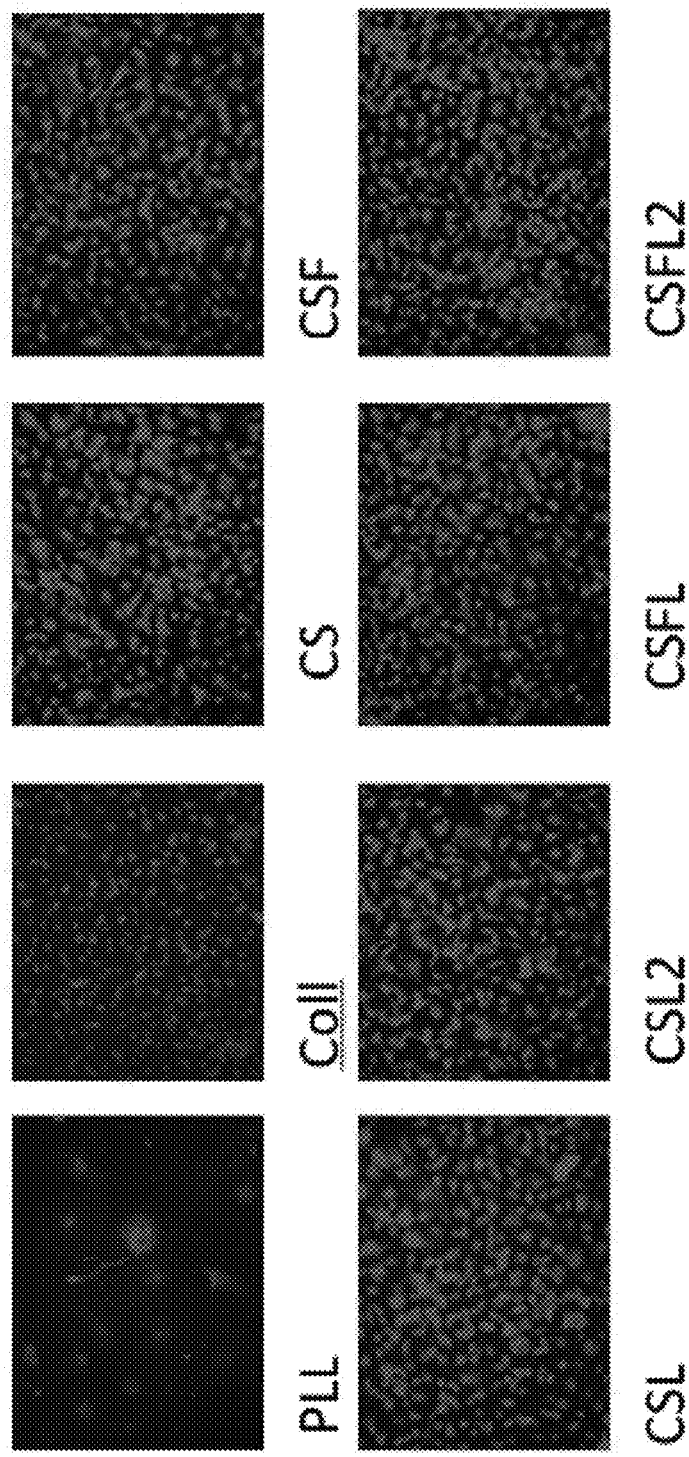
FIG. 10 illustrates S42 cells cultured on well-plates coated with a range of macromolecules for 7 days. The cells were stained with glial fibrillar acid protein (GFAP-red) characteristic of Schwann cells and Hoechst (nuclei-blue).

The conduits were tested to determine their ability to resist repeated compression from surrounding tissues. To achieve this, the conduits were tested for compression resistance and rebound force in a cyclic compression environment. A 10 mm conduit was hydrated for 1 hour in PBS before testing was carried out. The conduit was then placed on the lower platen (attached to a transparent trough) of the Zwick machine ensuring that it was lying at the center of the platen. The upper platen was then lowered so that the conduit was held between the 2 platens. The trough was then filled with PBS ensuring that the upper platen was visible below the water level. The Zwick machine was set up so that the conduit compressed to 50% of its original diameter at a rate of 30 mm/min in a cyclic manner. 100 cycles were run on each sample. The load cell of the Zwick machine recorded the force required to compress the conduit in the compression cycle and the rebounding force exerted by the conduit during the relaxation cycle. See FIGS. 8 and 9. It was evident that the conduits were capable of rebounding with minimal displacement of their diameters (FIG. 8). There was also minimal change in their force required to compress the conduits when we compared the first and hundredth cycles of compression (FIG. 9). Importantly, the samples maintained over 90% of their original rebound force after 100 cycles. This highlights their high degree of fatigue resistance in compressive environments.

Example 10

The conduits were imaged using SEM to determine the pore architecture and interaction between the hollow conduit and internal matrix. Both the hollow and filled conduits were sliced at two orientations—cross-sections and longitudinal sections. In some cases, the internal matrix was produced alone, without the hollow conduit, so as to determine the degree of alignment of pores. These samples were also sliced into cross-sections and longitudinal sections. Pore size analysis was carried out manually using ImageJ. Clamp a 2 cm×2 cm piece of PTFE tape onto the workbench. Place the sample or conduit onto the tape and hold in place with forceps to prevent movement. Using a new Wilkinson Sword razor blade, slowly slice the sample into the required orientation making exaggerated slicing movements so that the blade is worked from one end of the sharp edge to the other. Having sliced the sample as required, use the same blade to detach it from the PTFE tape, rather than using forceps which can cause tears. Place the samples into vials for storage at room temperature. The table below includes the raw data from the pore size analysis on SEM images. See FIGS. 5A-D and FIGS. 6A-D.

| Cross-section (um) | Ablumen (um) | Lumen (um) |
|---|---|---|
| 1 | 106.667 | 139.402 |
| 2 | 105.409 | 139.402 |
| 3 | 149.071 | 65.217 |
| 4 | 189.62 | 52.894 |
| 5 | 109.949 | 34.783 |
| 6 | 129.443 | 215.206 |
| 7 | 160.278 | 181.623 |
| 8 | 109.949 | 27.498 |
| 9 | 152.315 | 44.339 |
| 10 | 203.087 | 22.17 |
| 11 | 137.437 | 25.352 |
| 12 | 127.366 | 21.739 |
| 13 | 147.573 | 35.053 |
| 14 | 126.667 | 30.744 |
| 15 | 116.619 | 29.166 |
| 16 | 121.655 | 26.087 |
| 17 | 133.5 | 25.352 |
| 18 | 124.544 | 19.444 |
| 19 | 132.832 | 23.414 |
| 20 | 173.845 | 23.414 |

Example 11

Figure 7:
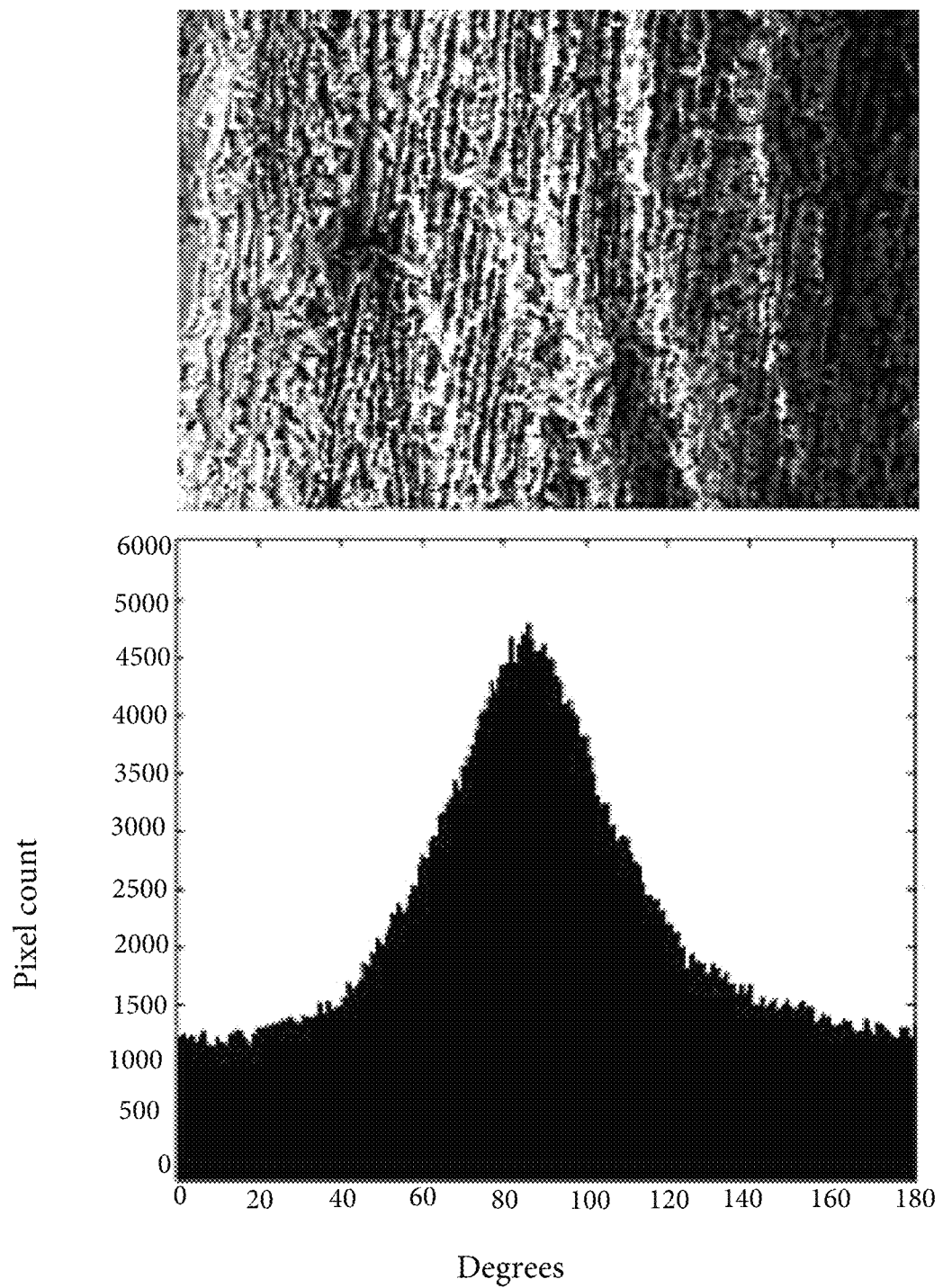
FIG. 7 is a graphical analysis of the internal matrices of the conduit prototype. The more pixels present at 90°, the more aligned the pores are axially. Pixels close to 0° and 180° represent pores that are perpendicular to the length of the conduit and therefore not aligned axially.

Pore alignment was assessed using a method based on a Matlab program stemming from the paper Meng Sun et al., 2015 (DOI: 10.1371/journal.pone.0131814) that assesses the pixel orientation of an image and gives a quantitative measure for this. The orientation is calculated in degrees. Pixel counts at 90 degrees represent parallel alignment whereas less/greater than 90 degrees represent deviation from alignment. The higher the count at 90 degrees therefore suggests greater alignment. FIG. 7 is a graphical analysis of the internal matrices of the conduit prototype. As discussed above, the more pixels present at 90°, the more aligned the pores are axially. Pixels close to 0° and 180° represent pores that are perpendicular to the length of the conduit and therefore not aligned axially. The fast_quantification_alignment.m is the main function that imports the image data. The image should either be in 8-bit or 16-bit. Change line 18 in the M.file 'fast_quantification_alignment.m' if using an 8-bit or 16-bit image as follows; blksze=15; thresh=0.5; thr=45 (for 8-bit) or thr=350 (for 16-bit). For optimal assessment, ensure that all the images are taken at the same magnification, resolution, contrast and of the same dimensions (x,y).

Example 12

Figure 11:
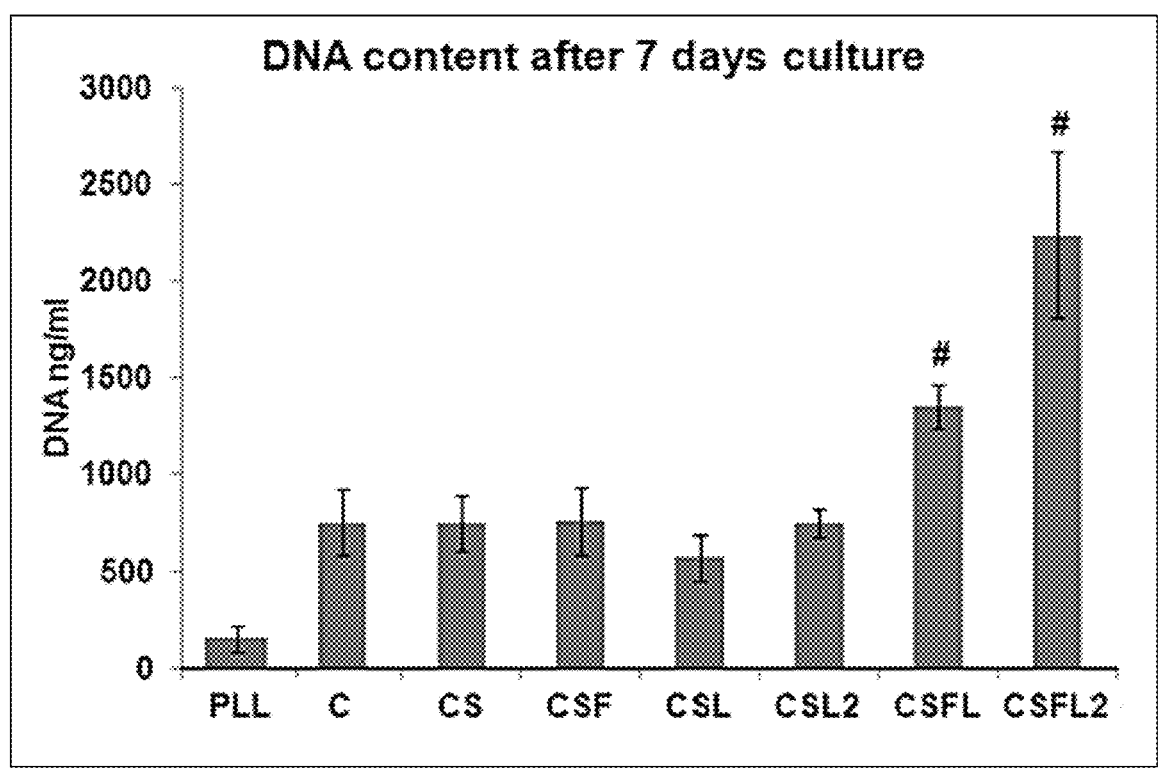
FIG. 11 depicts DNA content assessed after 7 days' culture of S42 Schwann cell line on well plates coated with a range of macromolecules. # denotes p<0.01 statistical significant difference between CSFL or CSFL2 and all other groups.

In vitro assessment to determine the effect of the macromolecules on cellular response was carried out using a Schwann cell line (S42) that were purchased, as well as sciatic nerve explants and dorsal root ganglia that were isolated from rat tissue within the TERG labs. The desired macromolecules were coated on 6-well plates to assess the response of S42 Schwann cells. The S42 Schwann cells were then seeded onto the 6-well plates at a density of 5×10⁴ cells per well and the morphology and proliferation of the cells was assessed at 24/48 hours and 7 days respectively. Results indicate that the PLL group led to high cell spreading, but limited proliferation after 7 days. In contrast, the collagen coated groups led to greater cell spreading. Moreover, the presence of fibronectin and/or laminin-1 or -2 led to cells displaying more spindle-shaped morphologies which are characteristic of native Schwann cells. The presence of collagen and collagen-chondroitin sulfate led to over 3-fold increase in cell density compared to PLL after 7 days (FIG. 11). Moreover, when collagen was combined with fibronectin and laminin-1/-2, this led to even further increases by approximately 50% in cell density. The highest cell density was found in the CSFL2 group highlighting the potency of laminin-2 in cell proliferation.

| TREATMENT GROUPS | |
|---|---|
| PLL | Polylysine (50 µg/ml) (control) |
| C | Collagen (50 µg/ml) |
| CS | Collagen-chondroitin sulfate (collagen-50 µg/ml, cs-5 µg/ml) |
| CSF | Collagen-chondroitin sulfate-fibronectin (collagen-50 µg/ml, cs-5 µg/ml, fibronectin-5 µg/ml) |
| CSL | Collagen-chondroitin sulfate-laminin1 |
| CSL2 | Collagen-chondroitin sulfate-laminin2 |
| CSFL | Collagen-chondroitin sulfate-fibronectin-laminin1 |
| CSFL2 | Collagen-chondroitin sulfate-fibronectin-laminin2 |
| CSFLL2 | Collagen-chondroitin sulfate-fibronectin-laminin1-laminin2 |

Total macromolecule concentration - 5 µg/ml i.e. for a mixture of fibronectin & laminin1 - 2.5 µg/ml each so that there is a protein ratio of 1:1.

The same principle applies in terms of the ratio of macromolecules (1:1) incorporated if two proteins were utilized. However, the concentration of the internal matrix within the conduit was chosen initially as 25 µg/ml. There is some optimization required to be carried out before a final concentration is selected.

Dorsal root ganglia were cultured on three conduit types with internal matrices (CS, CSFL, CSFL2) for 7 days and assessed for Schwann cell and axonal growth within the conduits. It was evident that there was axonal outgrowth from the DRGs into the conduits by 7 days. There was also evidence of Schwann cell migration from the DRGs into the conduit. The presence of the axially aligned pores within the conduits permitted axons to sprout along the length of the pores thereby highlighting the importance of the physical guidance cues in the regenerative process.

It was evident that the conduits supported both Schwann cell and axonal growth into the internal matrices of the conduits. However, the composition influenced the depth of axonal penetration. Compared to the control, which represents the basic composition (collagen-chondroitin sulfate), the presence of the additional inductive macromolecules (fibronectin in combination with laminin-1/-2) led to enhanced axonal length. In particular, the conduits containing fibronectin and laminin-1 supported greater axonal penetration compared to the control conduit. The greatest axonal penetration was found in the conduits containing fibronectin and laminin-2 after 7 days (50% increase in cell density). See FIG. 10, FIG. 11, FIG. 14, and FIGS. 15A and 15B. Further, it was evident that there was an additive effect on cell proliferation as a result of the treatment with all 3 macromolecules. See FIG. 12. There was approximately 50% increase in proliferation between CSFL2 and CSFLL2 ($p<0.01$), and approximately 150% increase between CSFL and CSFLL2 ($p<0.01$). This demonstrates that combining all three macromolecules may have therapeutic potential in the early stages of the repair process by enhancing proliferation of Schwann cells.

The method to isolate the dorsal root ganglia follows. This protocol can be utilized for newly born or adult rats and is done under terminal anesthesia. Lay the rat on its side and, under a dissecting microscope, cut off the head at the cervical flexure and the tail just caudal to the hind limbs using micro-dissecting scissors. Remove the ventral (belly) portion of the rat to isolate the dorsal (back) structures containing the spinal cord. Position tissue dorsal side down and carefully remove any remaining viscera from the posterior wall. Place one blade of micro-dissecting scissors between vertebral column and spinal canal at rostral end and very carefully cut through vertebral column proceeding caudally, then tease apart the right and left halves of vertebral column to expose spinal cord and DRGs. Gently attempt to lift spinal cord from dorsal structures by grasping cord at rostral end while carefully "cutting" behind and around DRGs to sever adherent tissues. After isolating all spinal cords, pluck off DRGs using dissecting forceps and transfer to another 6-cm dish with ice-cold PBS. If nerve roots are present, they should be snipped away after removing DRGs from cords. Place the conduits, either sliced into cross-/longitudinal-sections or as whole conduits into a 24 well plate. Place the DRGs directly onto conduits. Culture with DMEM-F12 media supplemented with 10% FBS and 1% penicillin/streptomycin.

Figure 13:
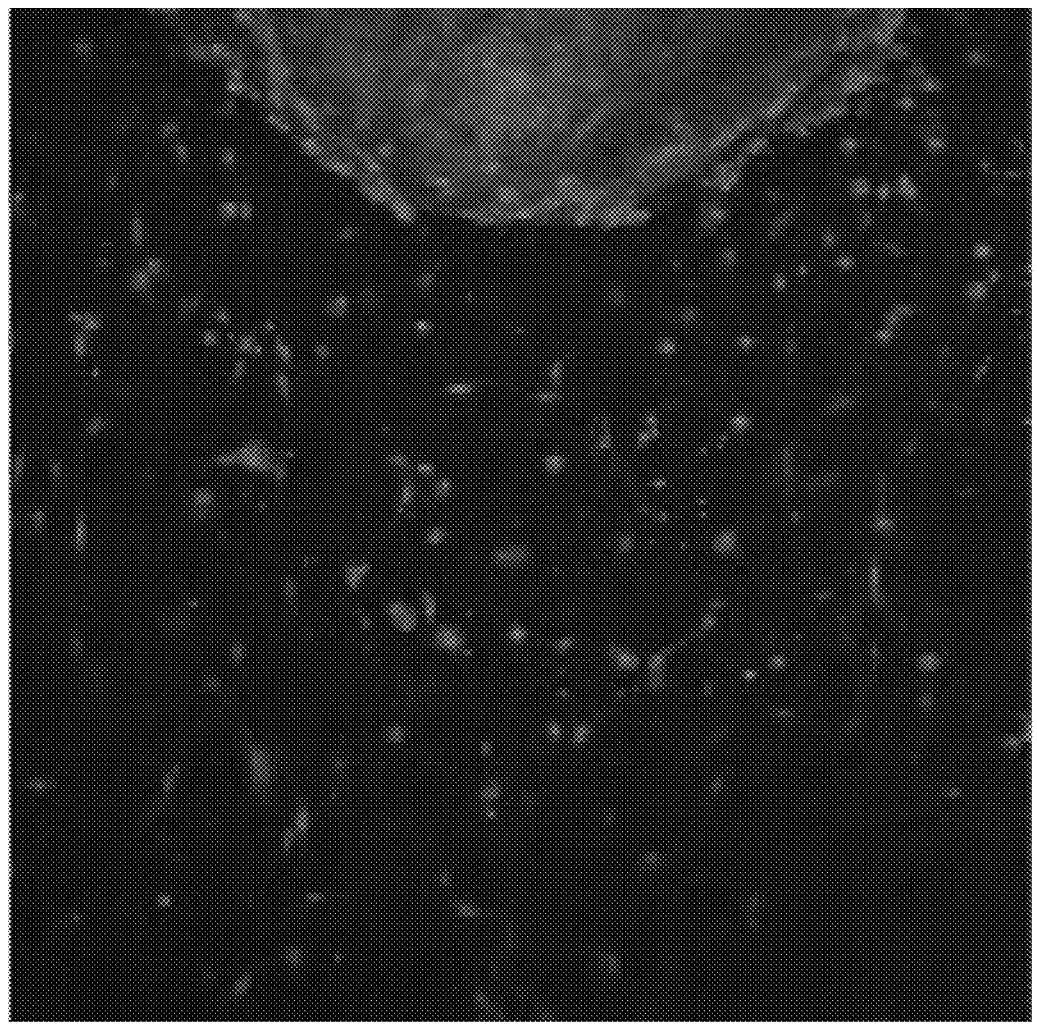
FIG. 13 illustrates Schwann cell migration from sciatic nerve explants into the filled conduits after 7 days' culture. The red cells show positive staining for S100b. The nuclei were stained blue with Hoechst.
Figure 14:
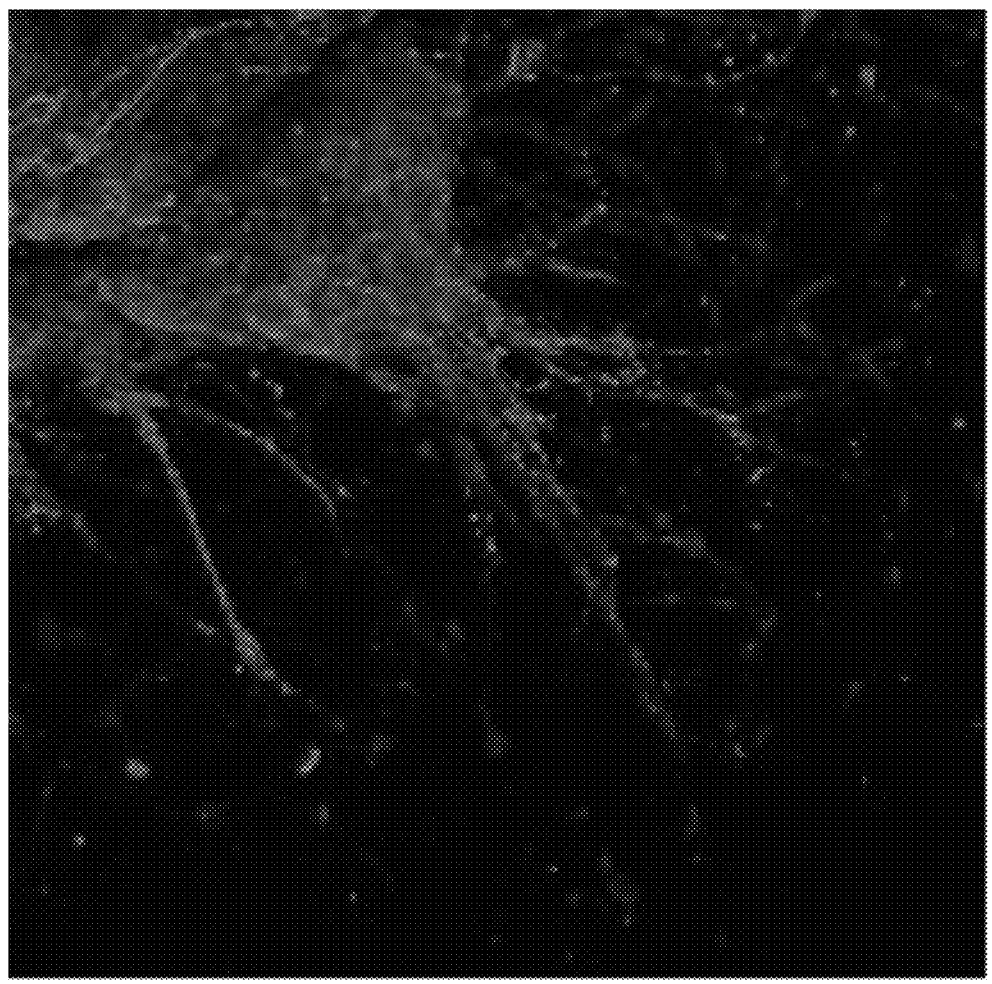
FIG. 14 illustrates dorsal root ganglia cultured on filled conduits (CS) for 7 days. Red staining is positive for axons and Schwann cells. Nuclei of cells are stained blue with Hoechst.
Figure 15A:
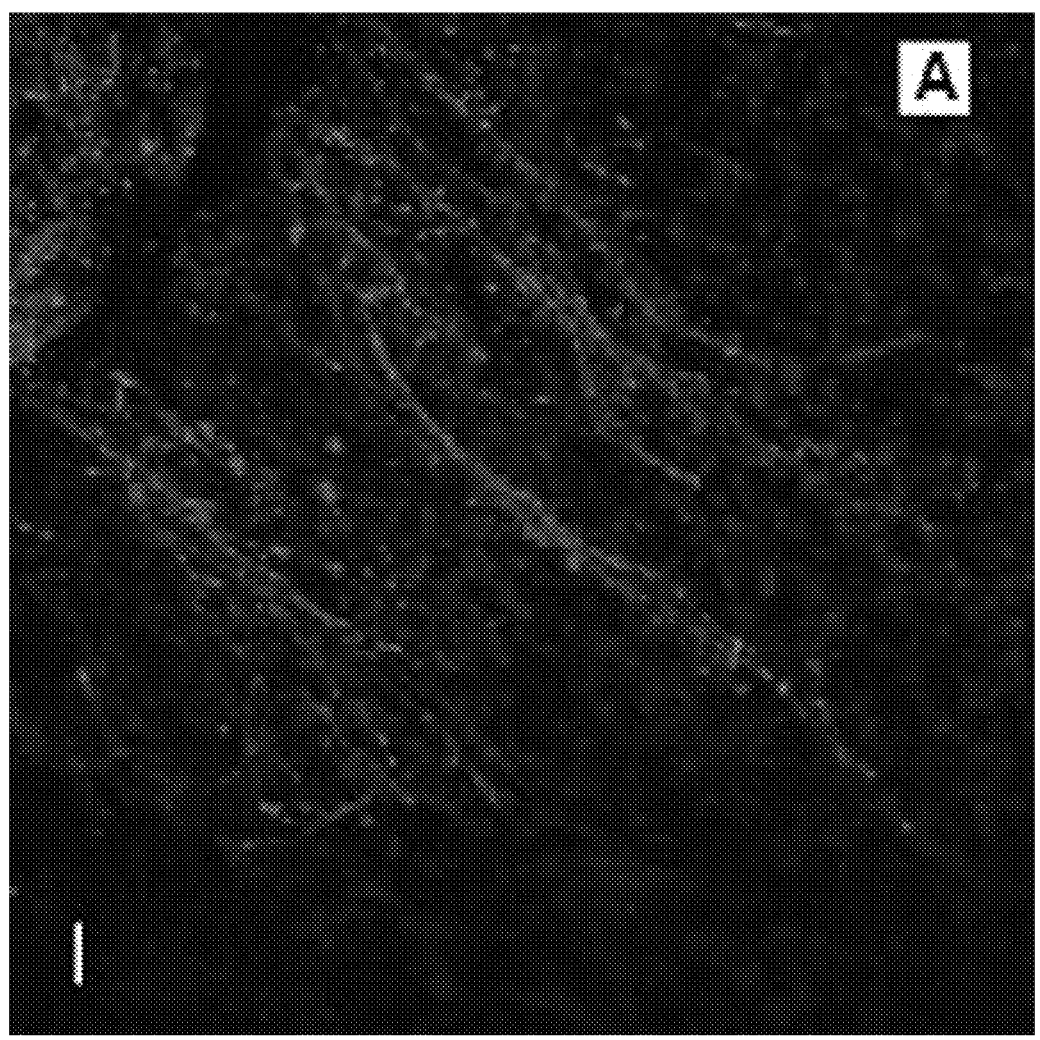
FIGS. 15A-B illustrate dorsal root ganglia cultured on filled conduits with internal matrices composed of CSFL (FIG. 15A) and CSFL2 (FIG. 15B) for 7 days. Red staining is positive for axons and Schwann cells. Nuclei of cells are stained blue.
Figure 15B:
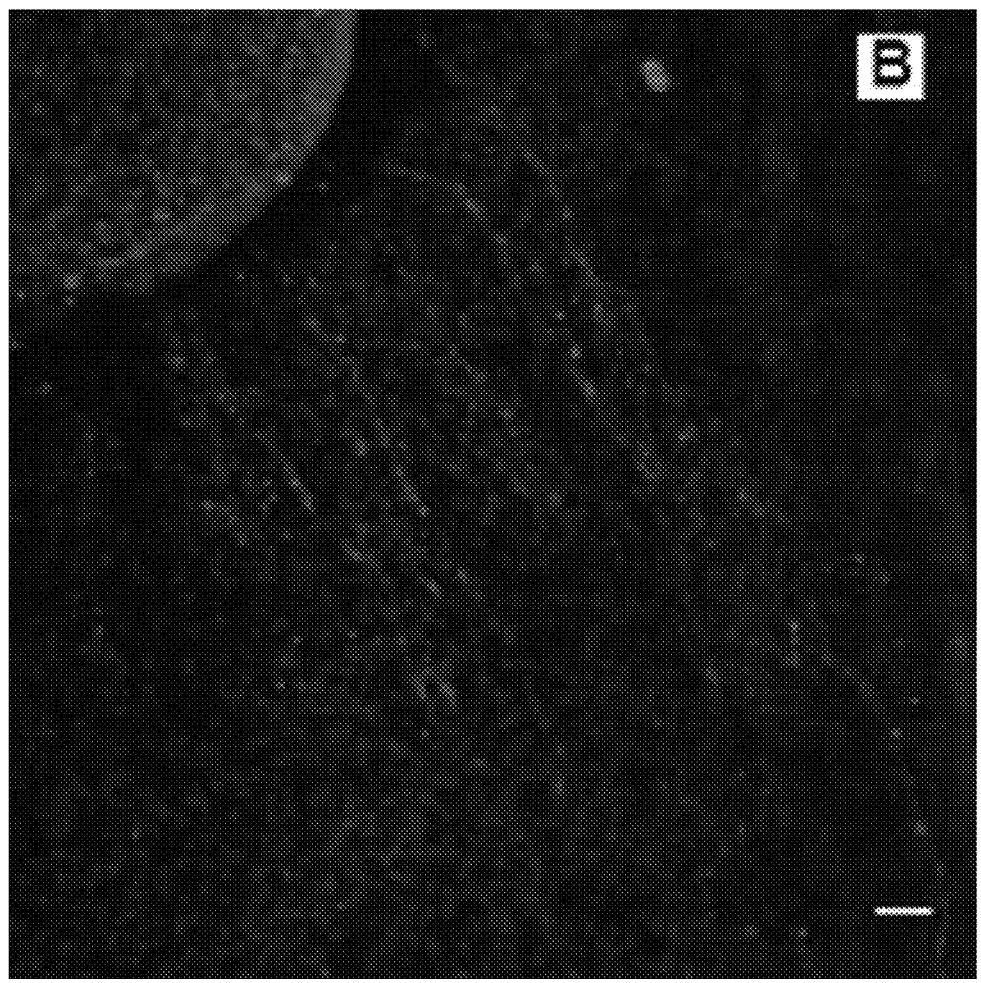

Sciatic nerve explants were sliced into approximately 2 mm segments and cultured directly onto the filled conduits. Assessment of cell migration from the conduits was subsequently carried out. The sciatic nerve explant can be seen at the top of FIG. 13 and the blue staining represents the nuclei of migrating cells from the sciatic nerve explants after 7 days. There was evidence of Schwann cells within the conduit as demonstrated by the positive red staining thereby demonstrating the ability of the conduit to permit Schwann cell migration from the explants. Comparing the three conduit type (CS, CSFL, CSFL2), there was no difference in the migration capacity of Schwann cells from the conduits.

The method used to isolate the sciatic nerve tissue is described next. This procedure is done under terminal anesthesia. Shave the fur from the rat and place the animal on a surgical board in the prone position and secure the front and hind legs to the board. Using a scalpel, make an incision on the leg of the rat. Separate the skin from the muscle and fascia. Slowly separate the interval between the biceps femoris and the superficial gluteal muscles with scissors until the sciatic nerve is exposed. Cut back the muscle along the skin incision line so that the majority of sciatic nerve is visible. Use scissors to cut off the nerve on both ends. Place the nerve on a petri-dish containing ice-cold PBS. Transfer to a tissue culture flow hood and cut the nerve into 2 mm segments and culture onto the conduits/desired samples with high glucose DMEM supplemented with 10% FBS and 1% penicillin/streptomycin.

Samples were stained using immunofluorescence in the following described method. Fix samples in 5% formalin for 1 hour and replace the formalin with PBS for storage overnight. Prepare the blocking buffer with 3% FBS, 0.3% Triton-X made up in PBS. Prepare dilution buffer with 1% FBS, 0.1% Triton-X made up in PBS. Wash the samples 3× in PBS. Incubate the samples in the blocking buffer for 30-60 minutes at room temperature. Do not wash the samples after the blocking buffer has been incubated. Apply the primary antibody made up in the dilution buffer at the desired concentration (Rabbit anti-rat Neurofilament 1:50; Mouse anti-rat S100β 1:50; Mouse anti-rat GFAP 1:40). Incubate at 4° C. overnight and then wash in PBS. Apply the secondary antibody made up in the dilution buffer at the desired concentration (Goat anti-mouse IgG Alexa448 1:500; Goat anti-rabbit IgG Alexa546 1:500). Incubate for 1 hour at 4° C. and then wash in PBS. Incubate in Hoechst 33342 at the desired concentration (1 µg/ml) diluted in PBS to stain for the nucleus. Store the samples at 4 C if not required immediately and ensure to cover in tin foil. See FIG. 10, FIG. 14 and FIGS. 15A and 15B.

Cell proliferation was determined by PicoGreen DNA assay. Reagents Required: Quant-iT PicoGreen dsDNA assay Molecular Probes P7589, 1% Triton-X buffer. Remove the 6-well plates from the incubator and apply 1% Triton-X and scrape off cells using a cell-scraper thoroughly. Place the solution into eppendorfs. Prepare a 1×TE solution from the 20× stock provided in the Quant-iT Kit (for each sample need 1.2 ml of 1×TE, for all standards need 6 ml of 1×TE). Prepare dilute PicoGreen solution, 200-fold dilution of DMSO stock (20 µl of PicoGreen in 3.98 ml of 1×TE is sufficient for standards and 5 samples, allow 350 µl for each additional sample). Dilute DNA stock (100 µg/ml) 50-fold to give 2 µg/ml (20 µl added to 980 µl 1×TE). Prepare DNA standards as follows:

| DNA Working Stock | 1 × TE | Final Concentration DNA/ml |
|---|---|---|
| 400 µl | 0 µl | 1000 ng |
| 200 µl | 200 µl | 500 ng |
| 100 µl | 300 µl | 250 ng |
| 40 µl | 360 µl | 100 ng |
| 20 µl | 380 µl | 50 ng |
| 10 µl | 390 µl | 25 ng |
| 4 µl | 396 µl | 10 ng |
| 0 µl | 400 µl | 0 ng |

Figure 12:
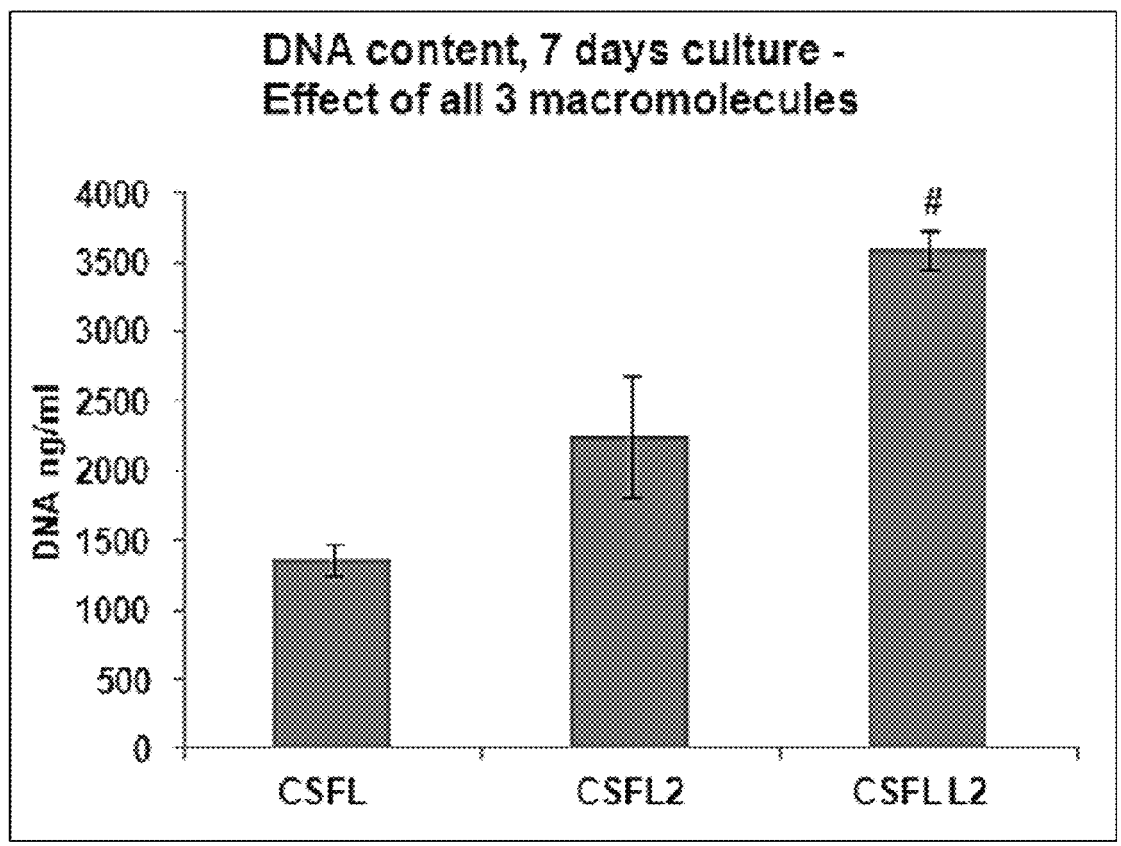
FIG. 12 depicts the effect of the combination of all 3 macromolecules on DNA content assessed after 7 days' culture of S42 Schwann cell line. # denotes p<0.01 statistical significant difference between CSFLL2 and all other groups.

Dilute samples 25× (16 µl sample+384 µl 1×TE). Add 100 µl of the appropriate standard to the wells of a 96-well plate or sample. All standards and samples to be assayed in triplicate. Add 100 µl of PicoGreen solution to each well and incubate at RT for 2-3 min. Read plate on fluorescent plate reader. Excite at 485 nm and read at 538 nm. FIGS. 11 and 12, and the table below summarize the total in vitro DNA content.

| Group | PLL | C | CS | CSF | CSL | CSL2 | CSFL | CSFL2 |
|---|---|---|---|---|---|---|---|---|
|  | 96.23984 | 863.0373 | 869.4763 | 858.894 | 597.08 | 756.925 | 1472.216 | 2743.867 |
|  | 188.5894 | 558.7809 | 802.057 | 884.0427 | 446.615 | 831.7972 | 1373.569 | 2074.91 |
|  | 96.8695 | 859.8953 | 597.4948 | 566.9837 | 688.0478 | 687.7629 | 1242.719 | 1932.061 |
| Avg. | 127.2329 | 760.5711 | 756.3427 | 769.9735 | 577.2476 | 758.8284 | 1362.835 | 2250.279 |
| St.dev. | 53.13723 | 174.7625 | 141.6363 | 176.2435 | 121.9321 | 72.03604 | 115.1246 | 433.3854 |

The data above demonstrated that laminins and fibronectin are essential in Schwann cell activity as well axonal growth. It was clear that the presence of both laminin-1/-2 as well as fibronectin led to elevated levels of cell proliferation. To be sure, when both laminins were used together in combination with fibronectin and collagen, the highest levels of proliferation were seen.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

REFERENCES

Bailey, S. B., Eichler, M. E., Villadiego, A. & Rich, K. M. 2003. The influence of fibronectin and laminin during Schwann cell migration and peripheral nerve regeneration through silicon chambers. *Journal of Neurocytology*, 22, 176-184.

Baron-Van Evercooren, A., Kleinman, H. K., Seppa, H. E., Rentier, B. & Dubois-Dalcq, M. 1982. Fibronectin promotes rat Schwann cell growth and motility. *The Journal of Cell Biology*, 93, 211-216.

Berti, C., Nodari, A., Wrabetz, L. & Feltri, M. L. 2006. Role of integrins in periphral nerves and hereditary neuropathies. *Neuromolecular Medicine*, 8, 191-204.

Bozkurt, A., Brook, G. A., Moellers, S., Lassner, F., Sellhaus, B., Weis, J., Woeltje, M., Tank, J., Beckmann, C., Fuchs, P., Damink, L. O., Schugner, F., Heschel, I. & Pallua, N. 2007. In vitro assessment of axonal growth using dorsal root ganglia explants in a novel three-dimensional collagen matrix. *Tissue Engineering*, 13, 2971-9.

Brattain, K. 2012. Analysis of the peripheral nerve repair market in the United States. Minneapolis: Magellan Medical Technology Consultants.

Bunge, M. B., Williams, A. K., Wood, P. M., Uitto, J. & Jeffrey, J. J. 1980. Comparison of nerve cell and nerve cell plus Schwann cell cultures, with particular emphasis on basal lamina and collagen formation. *Journal of Cell Biology*, 84, 184-202.

Bunge, R. P., Bunge, M. B. & Eldridge, C. F. 1986. Linkage between axonal ensheathment and basal lamina production by Schwann cells. *Annual Review of Neuroscience*, 9, 305-28.

Bunge M. B. (1993) Schwann cell regulation of extracellular matrix biosynthesis and assembly, In: Dyck P. J., Thomas P. K., Griffin J., Low P. A., and Poduslo J. F. (eds.). *Peripheral Neuropathy*, Philadelphia: W.B. Saunders, pp. 299-316.

Buttery, P. C. & ffrench-Constant, C. 1999. Laminin-2/integrin interactions enhance myelin membrane formation by oligodendrocytes. *Molecular and Cellular Neurosciences*, 14, 199-212.

Chang, H.-M., Shyu, M.-K., Tseng, G.-F., Liu, C.-H., Chang, H.-S., Lan, C.-T., Hsu, W.-M. & Liao, W.-C. 2013. Neuregulin facilitates nerve regeneration by speeding Schwann cell migration via ErbB2/3-dependent FAK pathway. *PLoS ONE*, 8, e53444.

Daly, W. T., Yao, L., Abu-rub, M. T., O'Connell, C., Zeugolis, D. I., Windebank, A. J. & Pandit, A. S. 2012. The effect of intraluminal contact mediated guidance signals on axonal mismatch during peripheral nerve repair. *Biomaterials*, 33, 6660-71.

Deumens, R., Bozkurt, A., Meek, M. F., Marcus, M. A., Joosten, E. A., Weis, J. & Brook, G. A. 2010. Repairing injured peripheral nerves: Bridging the gap. *Prog Neurobiol*, 92, 245-76.

Dubový, P., Svíženská, I., Klusáková, I., Zítková, A., Houšt'ava, L. & Haninec, P. 2001. Laminin molecules in freeze-treated nerve segments are associated with migrating Schwann cells that display the corresponding α6β1 integrin receptor. *Glia*, 33, 36-44.

Fex, S. A. & Dahlin, L. B. 2012. Repair of the Peripheral Nerve-Remyelination that Works. *Brain sciences,* 3, 1182-1197.

Fischer-Hayes, L. R., Brotherton, T. & Glass, J. D. 2013. Axonal degeneration in the peripheral nervous system: implications for the pathogenesis of amyotrophic lateral sclerosis. *Exp Neurol,* 246, 6-13.

Frost, E. E., Buttery, P. C., Milner, R. & ffrench-Constant, C. 1999. Integrins mediate a neuronal survival signal for oligodendrocytes. *Current Biology,* 9, 1251-S1.

Gao, X., Wang, Y., Chen, J. & Peng, J. 2013. The role of peripheral nerve ECM components in the tissue engineering nerve construction. *Rev Neurosci,* 24, 443-53.

Hasler, R. M., Exadaktylos, A. K., Bouamra, O., Benneker, L. M., Clancy, M., Sieber, R., Zimmermann, H. & Lecky, F. 2011. Epidemiology and predictors of spinal injury in adult major trauma patients: European cohort study. *Eur Spine J,* 20, 2174-80.

Kehoe, S., Zhang, X. F. & Boyd, D. 2012. FDA approved guidance conduits and wraps for peripheral nerve injury: a review of materials and efficacy. *Injury,* 43, 553-72.

Lee, J. Y., Giusti, G., Friedrich, P. F., Archibald, S. J., Kemnitzer, J. E., Patel, J., Desai, N., Bishop, A. T. & Shin, A. Y. 2012. The effect of collagen nerve conduits filled with collagen-glycosaminoglycan matrix on peripheral motor nerve regeneration in a rat model. *J Bone Joint Surg Am,* 94, 2084-91.

Liu, J., Chau, C.-H., Liu, H., Jang, B. R., Li, X., Chan, Y.-S. & Shum, D. K. Y. 2006. Upregulation of chondroitin 6-sulphotransferase-1 facilitates Schwann cell migration during axonal growth. *Journal of Cell Science,* 119, 933-942.

Milner, R., Wilby, M., Nishimura, S., Boylen, K., Edwards, G., Fawcett, J., Streuli, C., Pytela, R. & ffrench-Constant, C. 1997. Division of labor of Schwann cell integrins during migration on peripheral nerve extracellular matrix ligands. *Dev Biol,* 185, 215-28.

Mu, L., Sobotka, S., Chen, J., Su, H., Sanders, I., Adler, C. H., Shill, H. A., Caviness, J. N., Samanta, J. E., Beach, T. G. & Arizona Parkinson's Disease, C. 2013. Alpha-synuclein pathology and axonal degeneration of the peripheral motor nerves innervating pharyngeal muscles in Parkinson disease. *J Neuropathol Exp Neurol,* 72, 119-29.

Nectow, A. R., Marra, K. G. & Kaplan, D. L. 2012. Biomaterials for the development of peripheral nerve guidance conduits. *Tissue Eng Part B Rev,* 18, 40-50.

Noble, J., Munro, C. A., Prasad, V. S. & Midha, R. 1998. Analysis of upper and lower extremity peripheral nerve injuries in a population of patients with multiple injuries. *J Trauma,* 45, 116-22.

Pfister, B. J., Gordon, T., Loverde, J. R., Kochar, A. S., Mackinnon, S. E. & Cullen, D. K. 2011. Biomedical engineering strategies for peripheral nerve repair: surgical applications, state of the art, and future challenges. *Crit Rev Biomed Eng,* 39, 81-124.

Robinson, L. R. 2000. Traumatic injury to peripheral nerves. *Muscle Nerve,* 23, 863-73.

van Noort, J. M., Baker, D. & Amor, S. 2012. Mechanisms in the development of multiple sclerosis lesions: reconciling autoimmune and neurodegenerative factors. *CNS Neurol Disord Drug Targets,* 11, 556-69.

Wallquist, W., Patarroyo, M., Thams, S., Carlstedt, T., Stark, B., Cullheim, S. & Hammarberg, H. 2002. Laminin chains in rat and human peripheral nerve: Distribution and regulation during development and after axonal injury. *The Journal of Comparative Neurology,* 454, 284-293.

Wallquist, W., Plantman, S., Thams, S., Thyboll, J., Kortesmaa, J., Lannergren, J., Domogatskaya, A., Ogren, S. O., Risling, M., Hammarberg, H., Tryggvason, K. & Cullheim, S. 2005. Impeded interaction between Schwann cells and axons in the absence of laminin alpha4. *Journal of Neuroscience,* 25, 3692-700.

What is claimed is:

1. A nerve guide conduit comprising:
   an outer collagen tube;
   an internal matrix formed within the outer collagen tube by filling the collagen tube with a slurry comprising collagen, glycosaminoglycan, fibronectin, laminin-1, and laminin-2, wherein the glycosaminoglycan, fibronectin, laminin-1, and laminin-2 have a dry weight basis in the ratio of about 1:1:1:1; freezing the slurry along an axial direction of the slurry, with the slurry having no detectable radial thermal gradient, to form a frozen slurry having parallel axially aligned crystals; and freeze drying the collagen tube and the frozen slurry to remove the parallel axially aligned crystals and form the internal matrix having parallel axially aligned internal matrix pores that span one end of the matrix to the other.

2. The nerve guide conduit of claim 1 wherein the step of freezing includes contacting a proximal end of the collagen tube to a heat sink with the slurry freezing from a proximal end of the slurry to a distal end of the slurry to form the frozen slurry.

3. The nerve guide conduit of claim 1 wherein the step of freezing the slurry comprises providing a cooling gradient in the axial direction of the slurry by heat transfer from the slurry to a cooling medium, wherein the cooling gradient has substantially no radial component.

4. The nerve guide conduit of claim 1 including the step of insulating the collagen tube to provide no detectable radial thermal gradient during the step of freezing the slurry.

5. The nerve guide conduit of claim 1 wherein the collagen tube is placed in a mold which is insulated.

6. The nerve guide conduit of claim 5 wherein the mold is a polystyrene block.

7. The nerve guide conduit of claim 1 wherein the step of freezing the slurry comprises heat transfer from the slurry to a cooling medium through a thermally conducting screw, plug, or pole contacting a proximal end of the collagen tube and the cooling medium, with the freezing moving from a proximal end of the slurry to the distal end of the slurry.

8. The nerve guide conduit of claim 1 wherein the internal matrix pores have an average diameter of about 10 μm to about 300 μm.

9. The nerve guide conduit of claim 1 wherein the collagen tube comprises pores with an average diameter of about 100 μm to about 200 μm.

10. The nerve guide conduit of claim 1 wherein the glycosaminoglycan is selected from the group consisting of chondroitin sulfate, dermatan sulfate, keratin sulfate, and hyaluronic acid.

11. The nerve guide conduit of claim 1 wherein freezing the slurry is performed using liquid nitrogen or dry ice.

12. The nerve guide conduit of claim 1 wherein the chondroitin sulfate, fibronectin, laminin-1, and laminin-2 each have a concentration of about 5 μg/ml in the slurry.

13. A nerve guide conduit comprising:
    an outer collagen tube; and
    an internal matrix within the outer collagen tube, the internal matrix comprising collagen, glycosaminoglycan, fibronectin, laminin-1, and laminin-2, and having parallel axially aligned internal matrix pores that span one end of the matrix to the other;

wherein the glycosaminoglycan, fibronectin, laminin-1, and laminin-2 have a dry weight basis in the ratio of about 1:1:1:1.

14. The nerve guide conduit of claim 13 wherein the internal matrix pores have an average diameter of about 10 μm to about 300 μm.

15. The nerve guide conduit of claim 13 wherein the collagen tube has an internal diameter from about 1.5 mm to about 5.0 mm.

16. The nerve guide conduit of claim 13 wherein the conduit has a length from about 1 cm to about 15 cm.

17. The nerve guide conduit of claim 13 wherein the collagen tube comprises pores with an average diameter of about 100 μm to about 200 μm.

18. The nerve guide conduit of claim 13 wherein the collagen tube has an abluminal surface, wherein the abluminal surface has an irregular surface pore structure.

19. The nerve guide conduit of claim 13, wherein the abluminal surface pores have an average diameter of about 20 μm to about 200 μm.

20. The nerve guide conduit of claim 13 wherein the glycosaminoglycan is selected from the group consisting of chondroitin sulfate, dermatan sulfate, keratin sulfate, and hyaluronic acid.

* * * * *